(12) United States Patent
Kovatchev et al.

(10) Patent No.: US 11,238,990 B2
(45) Date of Patent: Feb. 1, 2022

(54) SYSTEM, METHOD AND COMPUTER SIMULATION ENVIRONMENT FOR IN SILICO TRIALS IN PRE-DIABETES AND TYPE 2 DIABETES

(75) Inventors: Boris P. Kovatchev, Charlottesville, VA (US); Claudio Cobelli, Padua (IT); Chiara Dalla Man, Venice (IT)

(73) Assignee: University of Virginia Patent Foundation, Charlottesville, VA (US)

( * ) Notice: Subject to any disclaimer, the term of this patent is extended or adjusted under 35 U.S.C. 154(b) by 190 days.

(21) Appl. No.: 13/380,839

(22) PCT Filed: Jun. 25, 2010

(86) PCT No.: PCT/US2010/040097
§ 371 (c)(1),
(2), (4) Date: Feb. 10, 2012

(87) PCT Pub. No.: WO2010/151834
PCT Pub. Date: Dec. 29, 2010

(65) Prior Publication Data
US 2012/0130698 A1 May 24, 2012

Related U.S. Application Data

(60) Provisional application No. 61/220,839, filed on Jun. 26, 2009.

(51) Int. Cl.
*G16H 10/00* (2018.01)
*G16H 50/50* (2018.01)
(Continued)

(52) U.S. Cl.
CPC ........... *G16H 50/50* (2018.01); *A61B 5/4842* (2013.01); *A61B 5/7275* (2013.01); *G06N 5/00* (2013.01);
(Continued)

(58) Field of Classification Search
CPC .. G06F 19/3437; G06F 19/3456; A61B 19/50
See application file for complete search history.

(56) References Cited

U.S. PATENT DOCUMENTS

2005/0197785 A1  9/2005 Polidori et al.
2009/0070088 A1  3/2009 Brahznik et al.

FOREIGN PATENT DOCUMENTS

WO  2008157781 A1  12/2008

OTHER PUBLICATIONS

Magni et al. (Journal of Diabetes Science and Technology, 2007, 1(6), 804-812).*

(Continued)

*Primary Examiner* — Lori A. Clow
*Assistant Examiner* — Marie Archer
(74) *Attorney, Agent, or Firm* — Potomac Law Group, PLLC; Vincent M DeLuca

(57) ABSTRACT

An electronic system is provided that simulates a glucose-insulin metabolic system of a T2DM or prediabetic subject, wherein the system includes a subsystem that models dynamic glucose concentration in a T2DM or prediabetic subject, including an electronic module that models endogenous glucose production (EGP(t)), or meal glucose rate of appearance (Ra(t>>, or glucose utilization (U(t)), or renal excretion of glucose (B(t)), a subsystem that models dynamic insulin concentration in said T2DM or prediabetic subject, including an electronic module that models insulin secretion (S(t)), an electronic database containing a population of virtual T2DM or prediabetic subjects, each virtual subject having a plurality of metabolic parameters, and a processing module that calculates an effect of variation of at least one metabolic parameter value on the glucose insulin metabolic system of a virtual subject by inputting the plurality of metabolic parameter values.

32 Claims, 7 Drawing Sheets

(51) Int. Cl.
*G16H 50/70* (2018.01)
*G06N 5/00* (2006.01)
*G16H 10/60* (2018.01)
*A61B 5/00* (2006.01)
*G16H 50/20* (2018.01)

(52) U.S. Cl.
CPC ............. *G16H 10/60* (2018.01); *G16H 50/20* (2018.01); *G16H 50/70* (2018.01)

(56) References Cited

OTHER PUBLICATIONS

Dalla Man, C., Rizza, R.A., Cobelli, C., "Meal Simulation Model of the Glucose-Insulin System," IEEE Transactions on Biomedical Engineering, vol. 54, No. 10, Oct. 2007.

Magni, L., Raimondo, D.M., Dalla Man, C., DeNicolao, G., Kovatchev, B., Cobelli, C., "Model Predictive Control of Glucose Concentration in Subjects with Type 1 Diabetes: An In Silico Trial," Proceedings of the 17th World Congress, The International Federation of Automatic Control, Seoul, Korea, Jul. 2008.

Boris P. Kovatchev et al., "In Silico Preclinical Trials: A Proof of Concept in Closed-Loop Control of Type 1 Diabetes", Journal of Diabetes Science and Technology, Jan. 1, 2009, pp. 44-55, XP055078894, Retrieved from the Internet: URL: http://www.ncbi.nlm.nih.gov/pmc/articles/PMC2681269/pdf/dst-03-0044.pdf, retrieved on Sep. 11, 2013.

The extended European Search Report dated Sep. 19, 2013.

Dalla Man et al.; "GIM, Simulation Software of Meal Glucose-Insulin Model"; Journal of diabetes science and technology, May 1, 2007; (May 1, 2007); Retrieved from the Internet: URL:http://journals.sagepub.com/doi/pdf/10.1177/193229680700100303; pp. 323-330.

* cited by examiner

SYSTEM, METHOD AND COMPUTER SIMULATION ENVIRONMENT FOR IN SILICO TRIALS IN PRE-DIABETES AND TYPE 2 DIABETES

BACKGROUND OF THE INVENTION

Over 20 million people in the United States alone have Type 2 Diabetes Mellitus (T2DM)—a complex derangement of the glucose-insulin metabolic system, which results in an increased insulin resistance and inappropriate insulin secretion. However, this pathological state does not appear suddenly, but usually subjects move from a healthy state to a diabetic state passing through an intermediate phase, called prediabetes: e.g. it is well known that individuals with impaired fasting glucose (IFG) have a 20-30% chance of developing diabetes over the following 5-10 years [1-3]. The risk is even greater if they have combined IFG and impaired glucose tolerance (IGT). Furthermore, IFG and IGT are associated with increased risk of cardiovascular events [4, 5]. Therefore, in addition to studies on T2DM, the pathogenesis of IFG alone or in combination with IGT has engendered considerable interest. For instance, recently, it has been shown that postprandial hyperglycemia in individuals with early diabetes is due to lower rates of glucose disappearance rather than increased meal appearance or impaired suppression of endogenous glucose production (EGP), regardless of their fasting glucose. In contrast, insulin secretion, action, and the pattern of postprandial turnover are essentially normal in individuals with isolated IFG [6]. These results suggest that for treatment and prevention of T2DM it is very important to provide drugs with a specific target, e.g. the ability to stimulate secretion instead of increasing insulin secretion, if this is the case.

To this purpose it is essential to investigate the mechanisms of glucose-inulin system derangement and drug pharmacodynamics, with properly designed experimental trials. However, it may not be possible, appropriate, convenient or desirable to perform such evaluation experiments on the diabetic subject in vivo, because some experiments cannot be done at all, or are too difficult, too dangerous, too expensive or not ethical. An in silica simulation environment could offer an alternative tool to test different treatment strategies, e.g. drug, exercise, diet, in prediabetes and diabetes in a cost-effective way. The power of simulation tools has been recently recognized by the FDA (Food and Drug Administration) which accepted a simulator of Type 1 Diabetes (T1DM) [7, 8] as an alternative to the animal studies for the validation of control algorithms before their use in human clinical trials [9]. No such simulator of T2DM has existed heretofore.

SUMMARY OF THE INVENTION

An aspect of an embodiment of the present invention extends the simulation of T1DM to T2DM. It is important to emphasize that due to the profound physiological differences between T1DM and T2DM, the mathematical model and the simulated "subjects" with T2DM are very different from the model and simulated "population" of T1DM.

Realistic computer simulation can provide invaluable information about the safety and the limitations of various treatments of T2DM, can guide and focus the emphasis of clinical studies, and can rule-out ineffective treatment scenarios in a cost-effective manner prior to human use. While simulators of diabetes exist, most are based on general population models. As a result, their capabilities are generally limited to prediction of population averages that would be observed during clinical trials.

Therefore, for the purpose of personalized treatment development, a different type of computer simulator is needed—a system that is capable of simulating the glucose-insulin dynamics of a particular person. In other words, a simulator of T2DM should be equipped with a "cohort" of in silico "subjects" that spans sufficiently well the observed inter-person variability of key metabolic parameters in the general population of people with T2DM. Because large-scale simulations would account better for inter-subject variability than small-size animal trials and would allow for more extensive testing of the limits and robustness of various treatments, the following paradigm has emerged: (i) in silico modeling could produce credible pre-clinical results that could be substituted for certain animal trials, and (ii) in silico testing yields these results in a fraction of the time required for animal trials.

Following this paradigm, this invention provides a comprehensive simulation environment, which has the potential to accelerate studies on T2DM and prediabetes. Two exemplary principal components of the simulation environment are: (1) A mathematical model of the human metabolic system which has been derived from a unique data set, including both T2DM and prediabetic patients who underwent a triple tracer meal protocol, and (2) A population of virtual subjects including N=100 subjects with pre-diabetes and N=100 subjects with T2DM. As previously demonstrated by our simulator of Type 1 Diabetes, a comprehensive simulation environment has the potential for performing rapid and cost-effective in silica experiments. T2DM specific experiments on virtual subjects could test the efficacy of drugs and other treatments, e.g. exercise or diet, for improving prediabetes and T2DM control.

In accordance with a first aspect of the invention, an electronic system is provided that simulates a glucose-insulin metabolic system of a T2DM or prediabetic subject, wherein the system includes a subsystem that models dynamic glucose concentration in a T2DM or prediabetic subject, including an electronic module that models endogenous glucose production (EGP(t)), an electronic module that models meal glucose rate of appearance (Ra(t)), an electronic module that models glucose utilization (U(t)), an electronic module that models renal excretion of glucose (E(t));

a subsystem that models dynamic insulin concentration in said T2DM or prediabetic subject, including an electronic module that models insulin secretion (S(t));

an electronic database containing a population of virtual T2DM or prediabetic subjects, each virtual subject having a plurality of metabolic parameters with values within a range of values derived from in vivo T2DM or prediabetic subjects; and a processing module that calculates an effect of variation of at least one metabolic parameter value on the glucose-insulin metabolic system of a virtual subject by inputting said plurality of metabolic parameter values including said at least one varied metabolic parameter value into said glucose concentration and insulin concentration subsystems.

In accordance with a second aspect of the invention, a computer-executable program product embodied as computer executable code in a computer-readable storage medium is provided, wherein said computer-executable program product simulates a glucose-insulin metabolic system of a T2DM or prediabetic subject, said computer-executable code including subsystem code that models dynamic glucose concentration in a T2DM or prediabetic subject, including an electronic code module that models endogenous glucose production (EGP(t)), an electronic code module that models meal glucose rate of appearance (Ra(t)), an electronic code module that models glucose utilization (U(t)), an electronic code module that models renal excretion of glucose (E(t));

subsystem code that models dynamic insulin concentration in said T2DM or prediabetic subject, including an electronic code module that models insulin secretion (S(t));

$$\begin{cases} \dot{G}_p(t) = EGP(t) + Ra(t) - U_{ii}(t) - E(t) - k_1 \cdot G_p(t) + k_2 \cdot G_t(t) & G_p(0) = G_{pb} \\ \dot{G}_t(t) = -U_{id}(t) + k_1 \cdot G_p(t) - k_2 \cdot G_t(t) & G_t(0) = G_{tb} \\ G(t) = \dfrac{G_p}{V_G} & G(0) = G_b \end{cases} \quad (1)$$

an electronic database containing a population of virtual T2DM or prediabetic subjects, each virtual subject having a plurality of metabolic parameters with values within a range of values derived from in vivo T2DM or prediabetic subjects; and computer-executable code that calculates an effect of variation of at least one metabolic parameter value on the glucose-insulin metabolic system of a virtual subject by inputting said plurality of metabolic parameter values including said at least one varied metabolic parameter value into said glucose concentration and insulin concentration subsystems.

DETAILED DESCRIPTION OF THE INVENTION

Figure 1A:
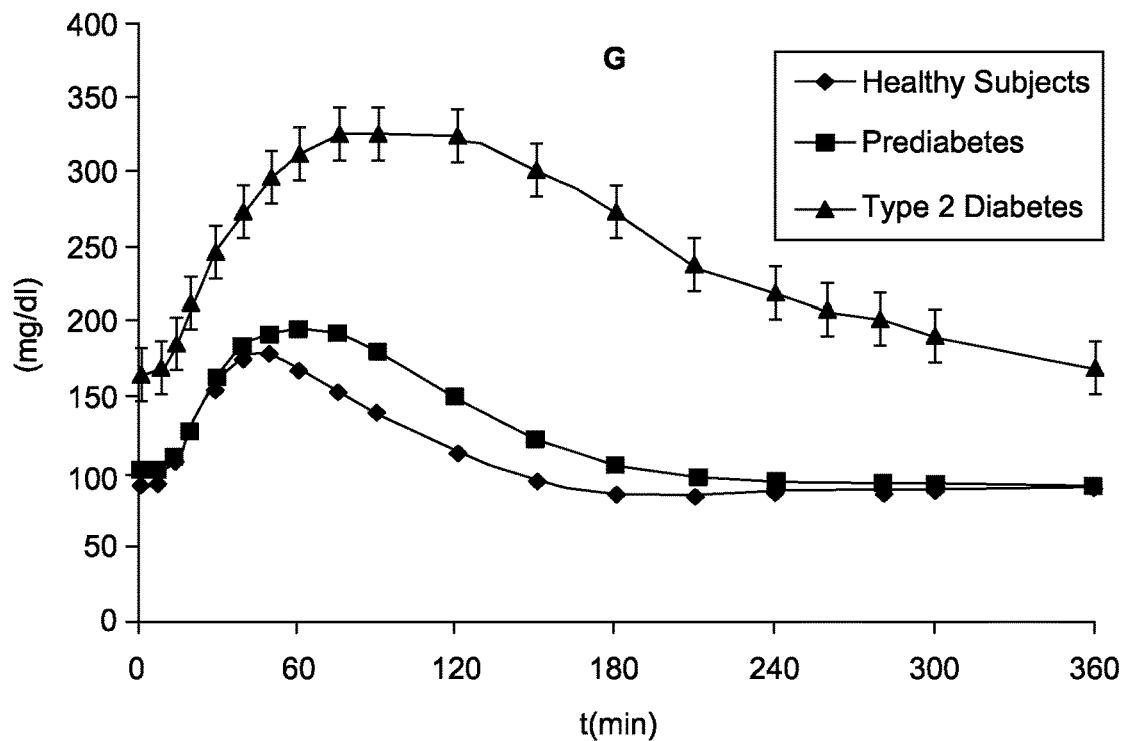
FIG. 1 is a set of graphs illustrating plasma glucose and insulin concentrations, meal rate of appearance and endogenous glucose production, and glucose utilization and insulin secretion rate.
Figure 1B:
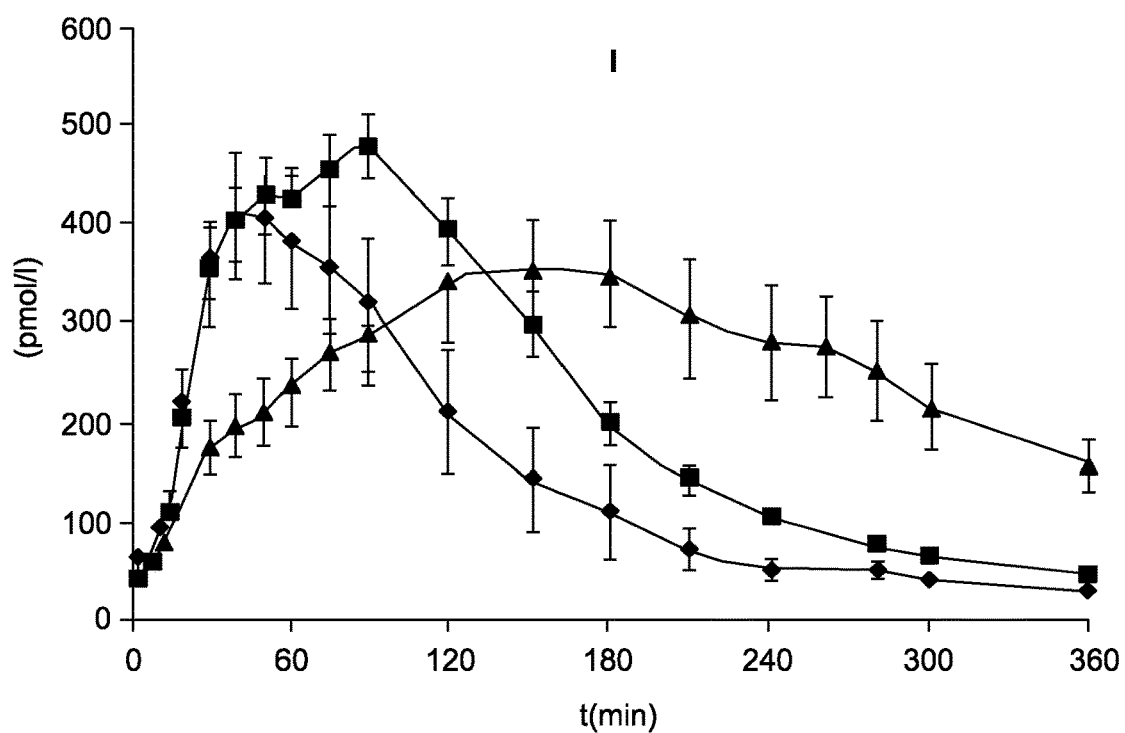
Figure 1C:
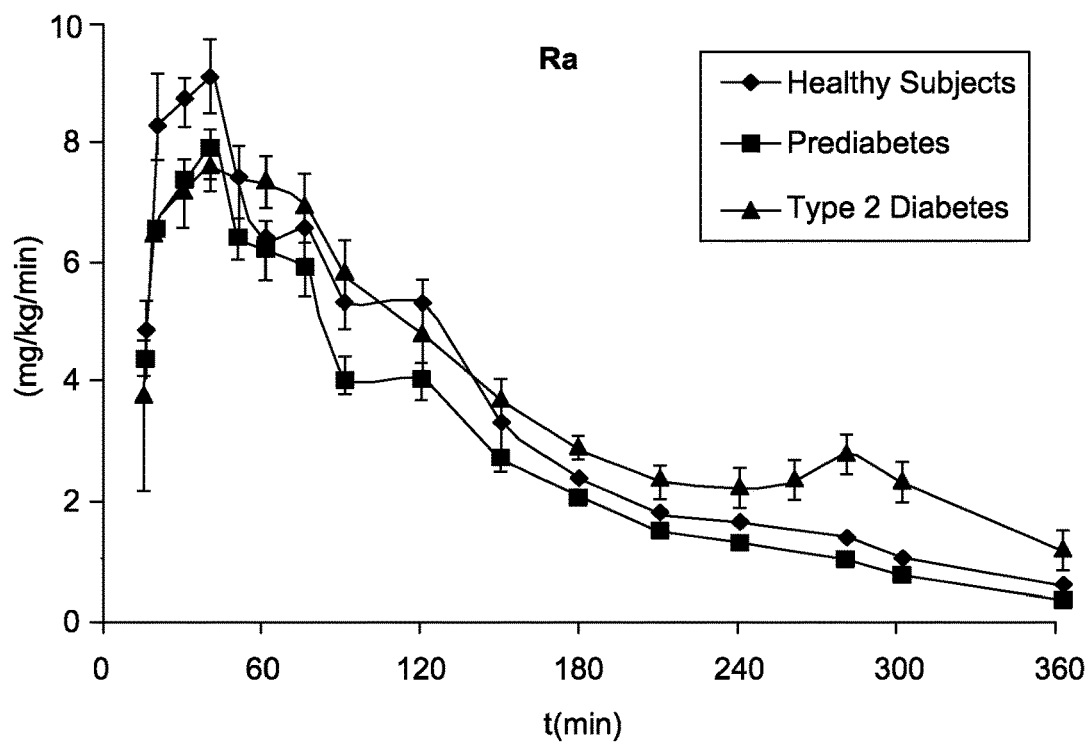
Figure 1D:
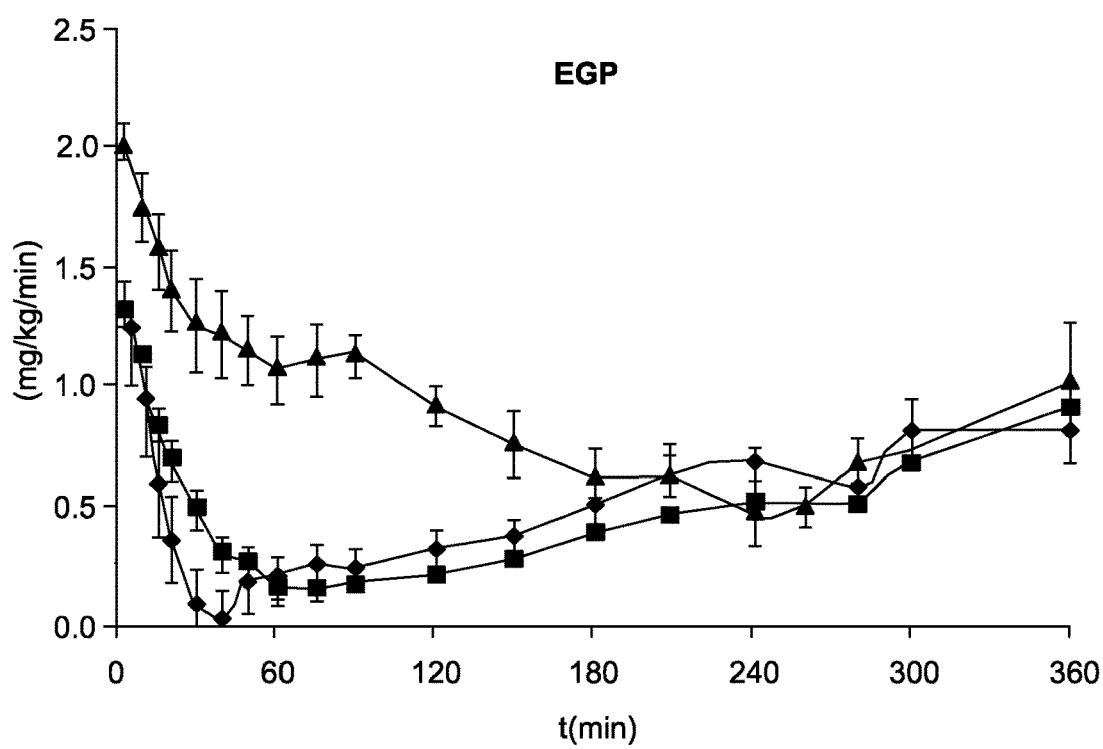
Figure 1E:
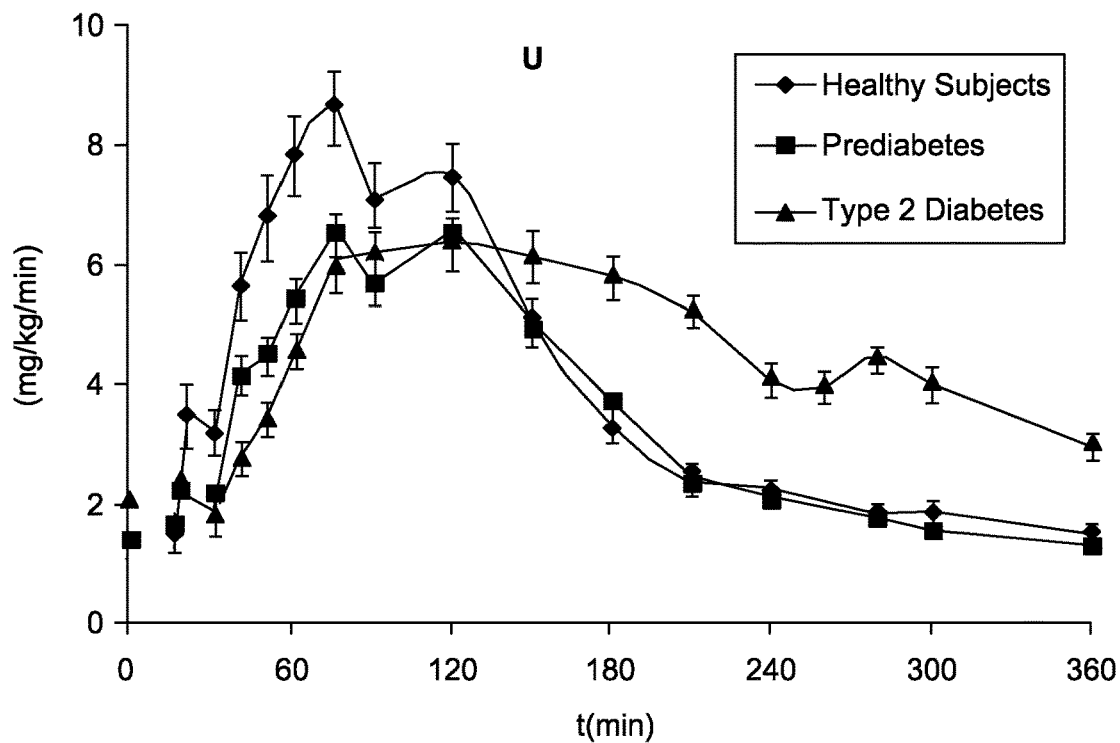
Figure 1F:
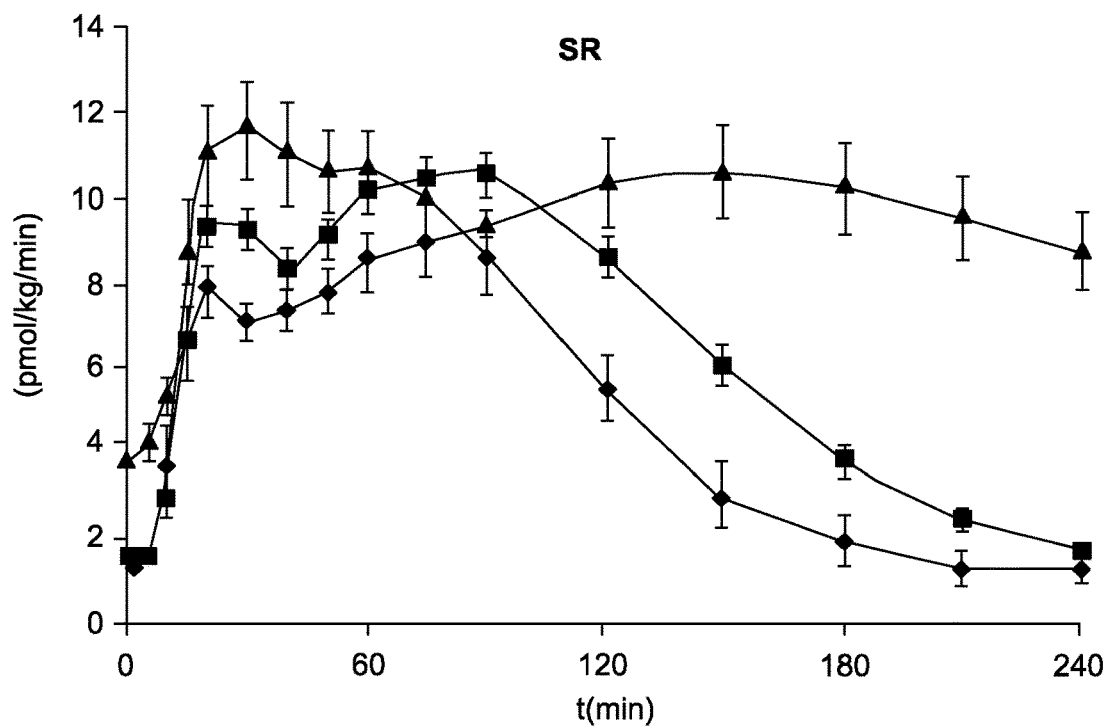

Two key components of the simulator of the glucose-insulin metabolic system in prediabetes and T2DM in accordance with the present invention are:

(1) A physiological model of glucose-insulin metabolism in prediabetes and T2DM, and (2) A population of virtual subjects with prediabetes (N=100) and T2DM (N=100).

Physiological Model of Glucose-Insulin Metabolism in Prediabetes and T2DM

Both model equations and the procedures which were used to identify model parameter distributions from prediabetes and T2DM meal data and to generate the virtual subject population are now described in accordance with an embodiment of the invention.

a. Model Equations

The model structure consists of a glucose subsystem and an insulin subsystem [7], each characterized by various unit processes, e.g. endogenous glucose production (EGP), meal glucose rate of appearance (Ra), glucose utilization (U), insulin secretion (S), and renal excretion (E).

Glucose Subsystem

The glucose subsystem model is defined by the following group of equations (1):

Where $G_p$ and $G_t$ (mg/kg) are glucose masses in plasma and rapidly-equilibrating tissues, and in slowly-equilibrating tissues, respectively;

G (mg/dl) is plasma glucose concentration;

Suffix b denotes the basal state;

EGP is endogenous glucose production (mg/kg/min);

Ra is glucose rate of appearance in plasma (mg/kg/min);

E is renal excretion (mg/kg/min);

$U_{ii}$ and $U_{id}$ are insulin-independent and dependent glucose utilizations, respectively (mg/kg/min);

$V_G$ is the distribution volume of glucose (dl/kg); and $k_1$ and $k_2$ ($\min^{-1}$) are rate parameters.

At the basal steady state, endogenous glucose production, $EGP_b$, equals glucose disappearance, i.e. the sum of glucose utilization and renal excretion (which is zero in normal subjects), $U_b + E_b$:

$$EGP_b = U_b + E_b \quad (2)$$

Insulin Subsystem

The insulin subsystem model is defined by the following group of equations (3):

$$\begin{cases} \dot{I}_l(t) = -(m_1 + m_3(t)) \cdot I_l(t) + m_2 I_p(t) + S(t) & I_l(0) = I_{lb} \\ \dot{I}_p(t) = -(m_2 + m_4) \cdot I_p(t) + m_1 \cdot I_l(t) & I_p(0) = I_{lb} \\ I(t) = \dfrac{I_p}{V_I} & I(0) = I_b \end{cases} \quad (3)$$

where $I_p$ and $I_l$ (pmol/kg) are insulin masses in plasma and in the liver, respectively;

I (pmol/l) is plasma insulin concentration;

S is insulin secretion (pmol/kg/min);

$V_I$ is the distribution volume of insulin (l/kg); and $m_1$-$m_4$ ($\min^{-1}$) are rate parameters.

Degradation, D, occurs both in the liver and peripherally. Peripheral degradation has been assumed to be linear ($m_4$). Hepatic extraction of insulin, HE, i.e. the insulin flux which leaves the liver irreversibly, divided by the total insulin flux leaving the liver, is assumed to be dependent from insulin secretion, S:

$$HE(t) = -m_5 \cdot S(t) + m_6 \; HE(0) = HE_b \quad (4)$$

thus one has:

$$m_3(t) = \frac{HE(t) \cdot m_1}{1 - HE(t)} \quad (5)$$

At basal steady state one has:

$$m_6 = m_5 \cdot S_b + HE_b \quad (6)$$

$$m_3(0) = \frac{HE_b \cdot m_1}{1 - HE_b} \quad (7)$$

$$S_b = m_3(0) \cdot I_{tb} + m_4 \cdot I_{pb} = D_b \quad (8)$$

Moreover, given that the liver is responsible for 60% of insulin clearance in the steady state, one has:

$$m_2 = \left(\frac{S_b}{I_{pb}} - \frac{m_4}{1 - HE_b}\right) \cdot \frac{1 - HE_b}{HE_b};$$

$$m_4 = \frac{2}{5} \cdot \frac{S_b}{I_{pb}} \cdot (1 - HE_b) \quad (9)$$

with $S_b$ and $D_b$ basal secretion and degradation, respectively ($HE_b$ was fixed to 0.6).

Endogenous Glucose Production

Endogenous glucose production is defined by the following equation (10):

$$EGP(t) = k_{p1} - k_{p2} \cdot G_p(t) - k_{p3} \cdot I_d(t) - k_{p4} \cdot I_{po}(t)$$
$$EGP(0) = EGP_b \quad (10)$$

where $I_{po}$ is the amount of insulin in the portal vein (pmol/kg);

$I_d$(pmol/l) is a delayed insulin signal realized with a chain of two compartments:

$$\begin{cases} \dot{I}_1(t) = -k_i \cdot [I_1(t) - I(t)] & I_1(0) = I_b \\ \dot{I}_d(t) = -k_i \cdot [I_d(t) - I_1(t)] & I_d(0) = I_b \end{cases} \quad (11)$$

$k_{p1}$ (mg/kg/min) is the extrapolated EGP at zero glucose and insulin;

$k_{p2}$ (min$^{-1}$) is liver glucose effectiveness;

$k_{p3}$ (mg/kg/min per pmol/l) is a parameter governing amplitude of insulin action on the liver;

$k_{p4}$ (mg/kg/min/(pmol/kg)) is a parameter governing amplitude of portal insulin action on the liver; and $k_i$ (min$^{-1}$) is a rate parameter accounting for the delay between an insulin signal and insulin action.

EGP is obviously constrained to be non-negative.

At basal steady state one has:

$$k_{p1} = EGP_b + k_{p2} \cdot G_{pb} + k_{p3} \cdot I_b + k_{p4} \cdot I_{pob} \quad (12)$$

Glucose Rate of Appearance

The glucose rate of appearance (Ra) is defined by the following group of equations (13):

$$\begin{cases} Q_{sto}(t) = Q_{sto1}(t) + Q_{sto2}(t) & Q_{sto}(0) = 0 \\ \dot{Q}_{sto1}(t) = -k_{gri} \cdot Q_{sto1}(t) + D \cdot \delta(t) & Q_{sto1}(0) = 0 \\ \dot{Q}_{sto2}(t) = -k_{empt}(Q_{sto}) \cdot Q_{sto2}(t) + k_{gri} \cdot Q_{sto1}(t) & Q_{sto2}(0) = 0 \\ \dot{Q}_{gut} = -k_{abs} \cdot Q_{gut}(t) + k_{empt}(Q_{sto}) \cdot Q_{sto2}(t) & Q_{gut}(0) = 0 \\ Ra(t) = \frac{f \cdot k_{abs} \cdot Q_{gut}(t)}{BW} & Ra(0) = 0 \end{cases} \quad (13)$$

where $Q_{sto}$ (mg) is the amount of glucose in the stomach (solid phase, $Q_{sto1}$, and liquid phase, $Q_{sto2}$);

$Q_{gut}$ (mg) is the glucose mass in the intestine;

$k_{gri}$(min$^{-1}$) is the rate of grinding;

$k_{empt}(Q_{sto})$ (min$^{-1}$) is a rate constant of gastric emptying which is a nonlinear function of $Q_{sto}$;

$k_{abs}$ (min$^{-1}$) is a rate constant of intestinal absorption;

f is a fraction of intestinal absorption which actually appears in the plasma;

D (mg) is an amount of ingested glucose;

BW (kg) is body weight; and

Ra (mg/kg/min) is the appearance rate of glucose in the plasma.

Glucose Utilization

Glucose utilization is made up of two components: insulin-independent utilization and insulin-dependent utilization. Insulin-independent utilization takes place in the first compartment, is constant and represents glucose uptake by the brain and erythrocytes ($F_{cns}$):

$$U_{ii}(t) = F_{cns} \quad (14)$$

Insulin-dependent utilization takes place in the remote compartment and depends nonlinearly (Michaelis Menten) from glucose in the tissues:

$$U_{id}(t) = \frac{V(X(t)) \cdot G_t(t)}{K_{m0} + G_t(t)} \quad (15)$$

where $Vm(X(t))$ is assumed to be linearly dependent from a remote insulin, $X(t)$:

$$V_m(X(t)) = V_{m0} + V_{mx} \cdot X(t) \quad (16)$$

X (pmol/L) is insulin in the interstitial fluid described by:

$$\dot{X}(t) = -p_{2U} \cdot X(t) + p_{2U}[I(t) - I_b] X(0) = 0 \quad (17)$$

where I is plasma insulin and $p_{2U}$ (min$^{-1}$) is rate constant of insulin action on the peripheral glucose utilization.

Total glucose utilization, U, is thus:

$$U(t) = U_{ii}(t) + U_{id}(t) \quad (18)$$

At basal steady state one has:

$$G_{tb} = \frac{F_{cns} - EGP_b + k_1 \cdot G_{pb}}{k_2} \quad (19)$$

and:

$$V_{m0} = \frac{(EGP_b - F_{cns}) \cdot (K_{m0} + G_{tb})}{G_{tb}} \quad (20)$$

Insulin Secretion

Insulin secretion, S, is defined by the following equations (21)-(24):

$$S(t) = \gamma \cdot I_{po}(t) \quad (21)$$

$$\dot{I}_{po}(t) = -\gamma \cdot I_{po}(t) + S_{po}(t) \quad I_{po}(0) = I_{pob} \quad (22)$$

$$S_{po}(t) = \begin{cases} Y(t) + K \cdot \dot{G}(t) + S_b & \text{for } \dot{G} > 0 \\ Y(t) + S_b & \text{for } \dot{G} \leq 0 \end{cases} \quad (23)$$

and $$\dot{Y}(t) = \begin{cases} -\alpha \cdot [Y(t) - \beta \cdot (G(t) - h)] & \text{if } \beta \cdot (G(t) - h) \geq -S_b \\ -\alpha \cdot Y(t) - \alpha \cdot S_b & \text{if } \beta \cdot (G(t) - h) < -S_b \end{cases} ; \quad (24)$$

$$Y(0) = 0$$

where $\gamma$ (min$^{-1}$) is the transfer rate constant between the portal vein and the liver;
K (pmol/kg per mg/dl) is the pancreatic responsivity to glucose rate of change;
a (min$^{-1}$) is the delay between the glucose signal and insulin secretion;
$\beta$ (pmol/kg/min per mg/dl) is the pancreatic responsivity to the glucose level; and
h (mg/dl) is the threshold level of glucose above which the $\beta$-cells initiate to produce new insulin (h was set to the basal glucose concentration $G_b$ to guarantee system steady state in basal condition).

Renal Glucose Excretion

Renal glucose excretion, E, is defined by the following equation (25):

$$E(t) = \begin{cases} k_{e1} \cdot [G_p(t) - k_{e2}] & \text{if } G_p(t) > k_{e2} \\ 0 & \text{if } G_p(t) \leq k_{e2} \end{cases} \quad (25)$$

where $k_{e1}$ (min$^{-1}$) is the glomerular filtration rate; and $k_{e2}$ (mg/kg) is the renal threshold of glucose.

b. Parameter Identification

The data base used to identify the model consisted of 35 subjects with either IFG or IGT, or both (prediabetes), and 23 T2DM patients who underwent a triple tracer meal protocol, thus allowing us to obtain in a virtually model-independent fashion the time course of all of the relevant glucose and insulin fluxes during a meal [6, 11]. Subject characteristics are reported in Table 1. Average plasma glucose and insulin concentration, Ra, EGP, U and SR in prediabetes and T2DM are shown in FIG. 1 together with the profile obtained in a matched healthy population [6]. In FIG. 1, plasma glucose and insulin concentrations are shown in the upper panels, meal glucose rate of appearance and endogenous glucose production are shown in the middle panels, and glucose utilization and insulin secretion rate are shown in the lower panels, in prediabetes, T2DM, and matched healthy subjects respectively.

TABLE 1

Anthropometric Characteristics of Prediabetes and Type 2 Diabetes

|  |  | Prediabetes | Type 2 Diabetes |
|---|---|---|---|
| Gender | (F/M) | 19/16 | 11/12 |
| Age | (years) | 53.4 | 56.1 |
| Weight | (kg) | 91.6 | 91.0 |
| BMI | (kg/m$^2$) | 30.4 | 31.8 |
| LBM | (kg) | 51.7 | 52.2 |
| % Fat | (%) | 37.8 | 38.6 |
| Visceral Fat | (cm$^2$) | 159.5 | 160.1 |

Figure 2:
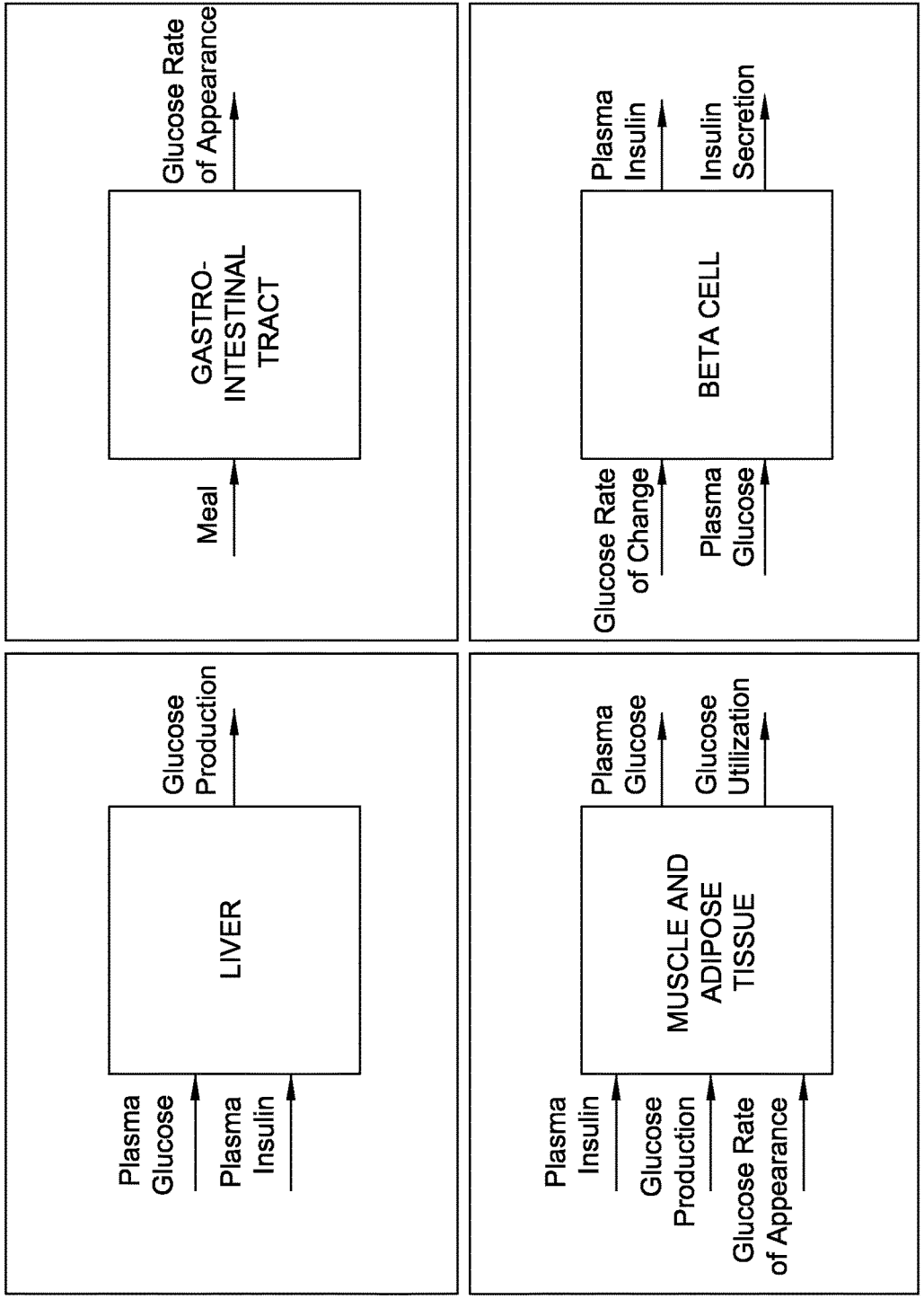
FIG. 2 illustrates unit process models for endogenous glucose production, glucose rate of appearance, glucose utilization, and insulin secretion in accordance with the present invention.

The system model described in section (a) has been identified in each subject by using a subsystem decomposition and forcing function strategy, as shown in FIG. 2. In FIG. 2, a unit process model for endogenous glucose production is shown in the top left panel; unit process model for glucose rate of appearance is shown in the top right panel; unit process model for glucose utilization is shown in the bottom left panel; an unit process model for insulin secretion is shown in the bottom right panel.

Entering arrows represent forcing function variables, and outgoing arrows are model output. For example, to estimate glucose utilization parameters (equations 14-20), we use as known inputs endogenous glucose production, EGP, glucose rate of appearance, Ra, and insulin concentration, I, and as the model output glucose utilization, U, and plasma glucose concentration, G.

Figure 3A:
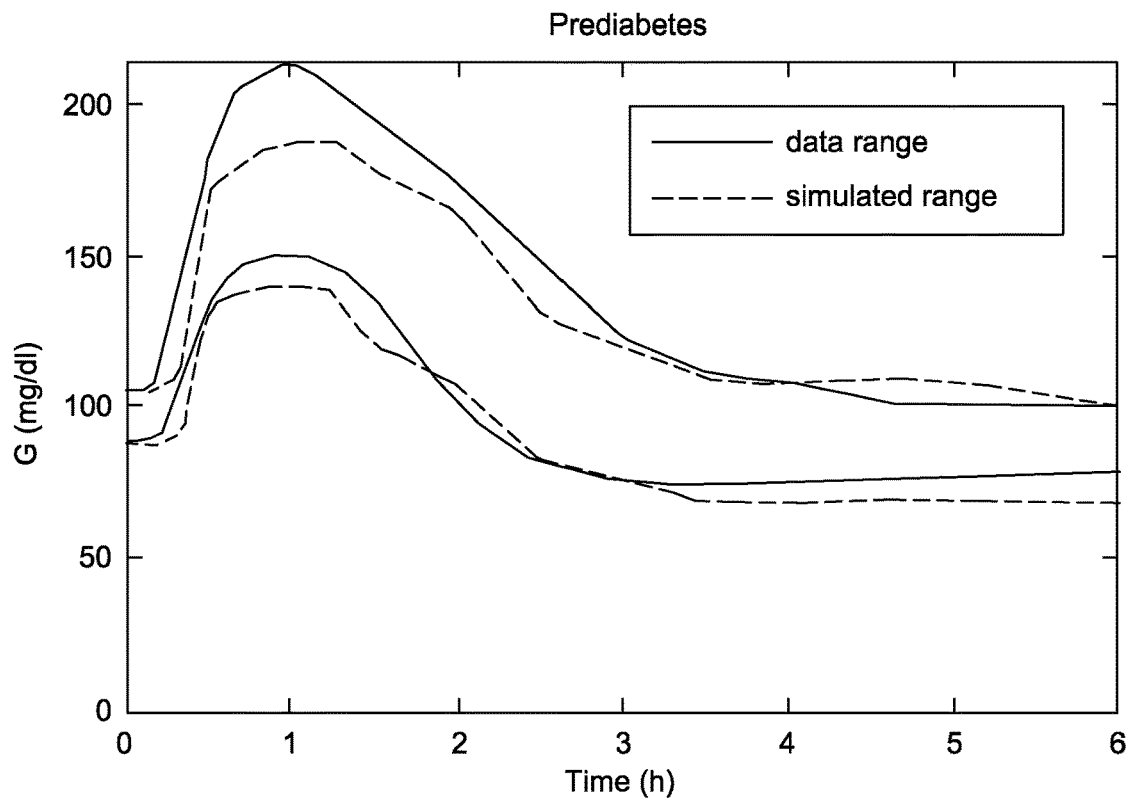
FIGS. 3A and 3B are graphs illustrating observed versus simulated range of glucose concentration in prediabetes and type 2 diabetes, in accordance with the present invention.
Figure 3B:
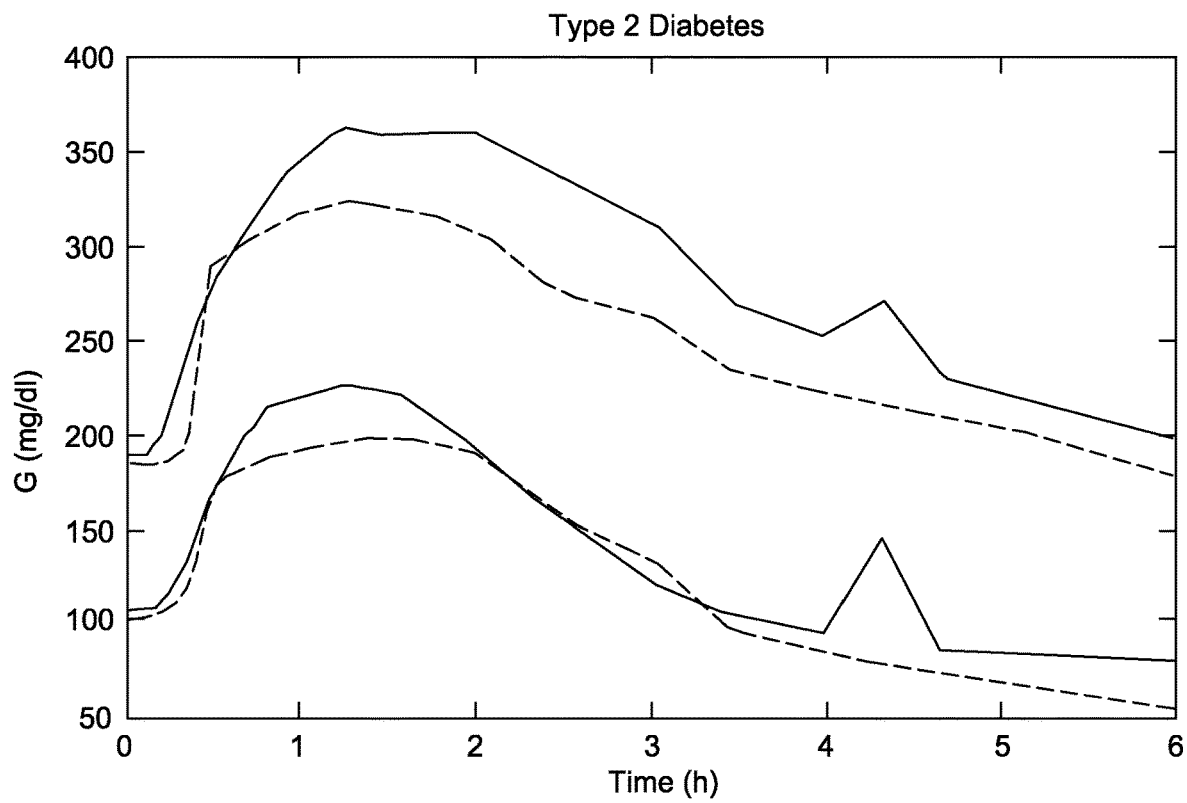

Model parameters were thus identified in each subject and log-transformed. The average parameter vector and the covariance matrix have been thus calculated for both prediabetic and T2DM populations. Assuming that the parameter vector is a log-normally distributed random vector, the average of log-transformed parameters and the covariance matrix univocally define the joint parameter distribution. In order to prove that the generated populations reflect the observed variability, the range of simulated plasma glucose concentrations in both populations (prediabetes and T2DM) is shown in FIG. 3, superimposed with the observed (measured) range of variability.

Figure 4A:
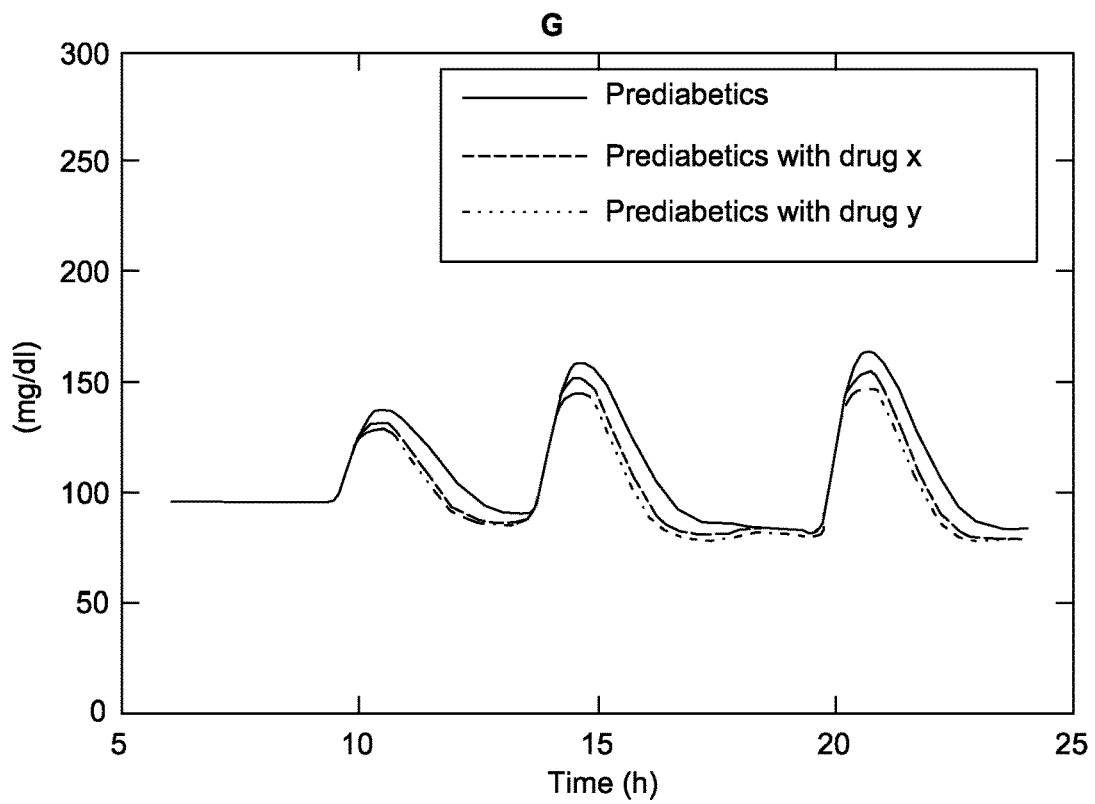
FIG. 4 illustrates glucose and insulin concentrations in untreated prediabetic subjects versus prediabetic subjects treated with drugs x and y.
Figure 4B:
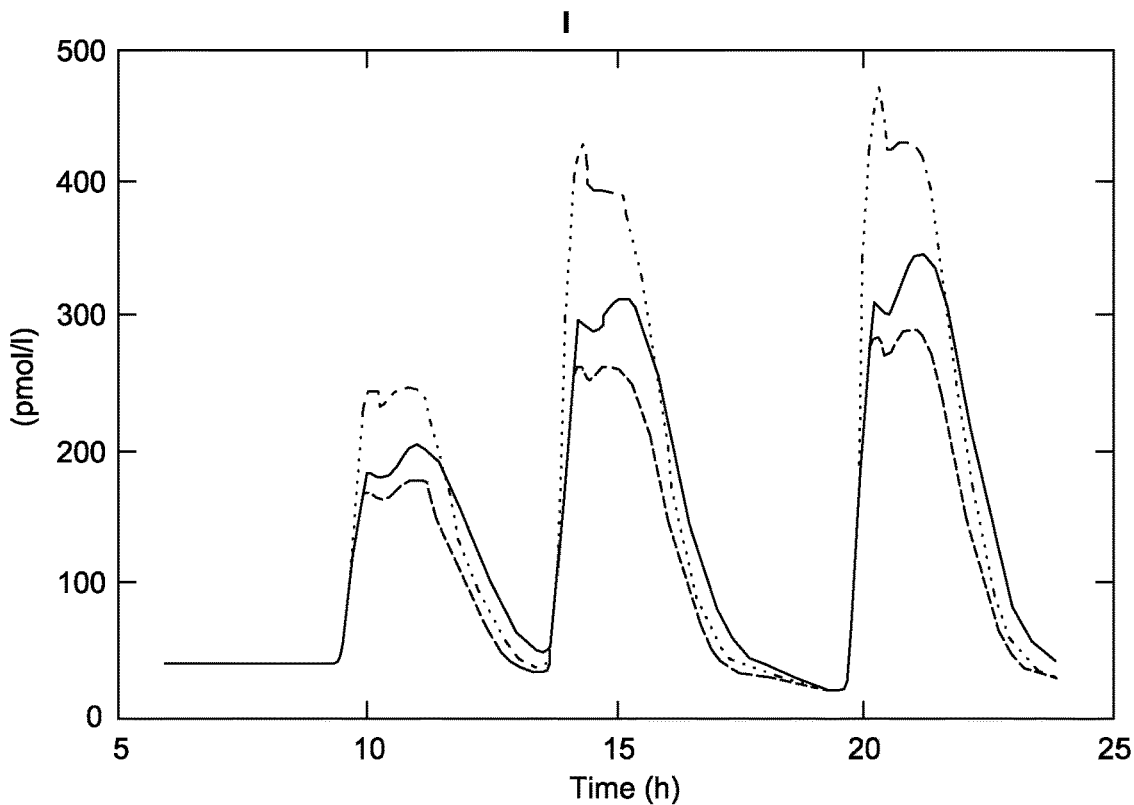

A potential application of the simulator is the in silico study of the effect of a drug on glucose metabolism. FIG. 4 shows plasma glucose and insulin concentrations in untreated prediabetics versus a profile obtained with the administration of a drug x, which increases insulin sensitivity, and a drug y, which enhance beta-cell responsivity to glucose.

Population of Virtual "Subjects" with Prediabetes (N=100) and T2DM (N=100).

As noted above, the key to successful simulation is the availability of a comprehensive population of simulated "subjects" that encompasses the distribution of key metabolic parameters observed in T2DM in vivo. From the joint parameter distributions described in the previous section we have generated N=200 virtual subjects: N=100 with prediabetes and N=100 with T2DM.

Each virtual subject is uniquely identified by a set of 26 parameters:

$k_{abs}$=rate constant of glucose absorption by the intestine
$k_{max}$=maximum rate constant of gastric emptying
$k_{min}$=minimum rate constant of gastric emptying
b=percentage of the dose for which $k_{empt}$ decreases at $(k_{max}-k_{min})/2$
c=percentage of the dose for which $k_{empt}$ is back to $(k_{max}-k_{min})/2$
$k_i$=rate parameter accounting for delay between insulin signal and insulin action on the liver
$k_{p2}$=liver glucose effectiveness $k_{p3}$=parameter governing amplitude of insulin action on the liver $k_{p4}$=parameter governing amplitude of portal insulin action on the liver $V_g$=distribution volume of glucose $V_{mx}$=parameter governing amplitude of insulin action on glucose utilization $k_{m0}$=parameter governing glucose control on glucose utilization $K_2$=rate parameter accounting for glucose transit from tissue to plasma $K_1$=rate parameter accounting for glucose transit from plasma to tissue $p_{2U}$=rate parameter accounting for delay between insulin signal and insulin action on glucose utilization $V_i$=distribution volume of insulin K=beta-cell responsivity to glucose rate of change β=beta-cell responsivity to glucose level α=rate parameter accounting for delay between glucose signal and insulin secretion $m_1$=rate parameter of insulin kinetics $m_5$=coefficient linking insulin hepatic extraction to insulin secretion rate $G_b$=basal plasma glucose concentration $EGP_b$=basal endogenous glucose production BW=body weight $I_b$=basal plasma insulin concentration $SR_b$=basal insulin secretion rate Provided below in Tables 2 and 3, are sample lists of model parameters for 10 pre-diabetes virtual subjects and 10 T2DM virtual subjects.

TABLE 2

Model Parameters in 10 Prediabetic Subjects

| parameter | unit | subj #1 | subj #2 | subj #3 | subj #4 | subj #5 | subj #6 | subj #7 | subj #8 | subj #9 | subj #10 |
|---|---|---|---|---|---|---|---|---|---|---|---|
| kabs | min^-1 | 0.0735 | 0.1099 | 0.1661 | 0.0729 | 0.0793 | 0.0356 | 0.1177 | 0.0297 | 0.0765 | 0.1105 |
| kmax | min^-1 | 0.0251 | 0.0292 | 0.0338 | 0.019 | 0.0354 | 0.036 | 0.0279 | 0.0314 | 0.0416 | 0.0315 |
| kmin | min^-1 | 0.0125 | 0.009 | 0.0081 | 0.0145 | 0.0085 | 0.0129 | 0.0139 | 0.0112 | 0.0073 | 0.0106 |
| b | dimensionless | 0.8197 | 0.6448 | 0.578 | 0.5239 | 0.6299 | 0.5467 | 0.6803 | 0.5534 | 0.5219 | 0.7486 |
| c | dimensionless | 0.0871 | 0.0783 | 0.0752 | 0.0514 | 0.0711 | 0.0194 | 0.061 | 0.0419 | 0.1386 | 0.0601 |
| ki | min^-1 | 0.0149 | 0.0112 | 0.007 | 0.0081 | 0.0077 | 0.0144 | 0.0083 | 0.0091 | 0.01 | 0.0089 |
| kp2 | min^-1 | 0.0023 | 0.0025 | 0.0032 | 0.0052 | 0.0107 | 0.0025 | 0.0048 | 0.0021 | 0.0024 | 0.0146 |
| kp3 | mg/kg/min/(pmol/l) | 0.0038 | 0.0035 | 0.0042 | 0.0201 | 0.0086 | 0.0124 | 0.0035 | 0.0103 | 0.0025 | 0.0041 |
| kp4 | mg/kg/min/(pmol/kg) | 0.0106 | 0.015 | 0.0298 | 0.0377 | 0.0218 | 0.0252 | 0.0144 | 0.0291 | 0.0119 | 0.0233 |
| Vg | dl/kg | 0.7703 | 1.5072 | 1.1806 | 1.35 | 1.2329 | 1.1499 | 1.4451 | 1.1974 | 1.417 | 1.151 |
| Vmx | mg/kg/min per pmol/L | 0.0762 | 0.0398 | 0.0219 | 0.1018 | 0.0224 | 0.1533 | 0.0103 | 0.0746 | 0.0111 | 0.0142 |
| km0 | mg/kg | 278.3481 | 262.9952 | 232.3868 | 285.9935 | 265.9869 | 306.6452 | 186.0311 | 317.4536 | 183.8099 | 194.9743 |
| K2 | min^-1 | 0.0987 | 0.0891 | 0.0641 | 0.1284 | 0.0512 | 0.0798 | 0.0506 | 0.0754 | 0.026 | 0.0396 |
| K1 | min^-1 | 0.1313 | 0.0917 | 0.0907 | 0.1006 | 0.0798 | 0.1316 | 0.0814 | 0.1402 | 0.0689 | 0.0854 |
| p2U | min^-1 | 0.084 | 0.0579 | 0.041 | 0.1024 | 0.0311 | 0.0383 | 0.0366 | 0.0688 | 0.0691 | 0.0303 |
| Vi | l/kg | 0.0465 | 0.0456 | 0.0456 | 0.0499 | 0.0449 | 0.047 | 0.048 | 0.0468 | 0.0476 | 0.0468 |
| K | pmol/kg/(mg/dl) | 2.7727 | 1.579 | 2.5114 | 1.2439 | 3.9261 | 2.2416 | 3.3872 | 1.2828 | 3.4512 | 4.1856 |
| β | pmol/kg/min/(mg/dl) | 0.2467 | 0.1839 | 0.1027 | 0.1169 | 0.0827 | 0.2034 | 0.1765 | 0.0905 | 0.148 | 0.1157 |
| α | min^-1 | 0.0163 | 0.0179 | 0.105 | 0.0263 | 0.115 | 0.0154 | 0.0504 | 0.0362 | 0.0494 | 0.045 |
| m1 | min^-1 | 0.0597 | 0.1086 | 0.1871 | 0.0805 | 0.2383 | 0.1657 | 0.1842 | 0.0845 | 0.2373 | 0.2718 |
| m5 | min * kg/pmol | 0.0163 | 0.0114 | 0.0164 | 0.0237 | 0.0276 | 0.0173 | 0.0085 | 0.0285 | 0.0205 | 0.0166 |
| Gb | mg/dl | 92.0683 | 110.7642 | 99.985 | 98.4865 | 88.3801 | 103.674 | 90.955 | 96.9737 | 87.9565 | 98.3493 |
| EGPb | mg/kg/min | 1.1875 | 1.2351 | 1.3047 | 1.9595 | 1.1917 | 1.199 | 1.412 | 1.3213 | 1.1577 | 1.14 |
| BW | kg | 74.0362 | 77.0909 | 94.1644 | 76.6412 | 123.5939 | 83.1689 | 84.8108 | 89.3894 | 106.9975 | 91.6455 |
| Ib | pmol/l | 22.9192 | 39.453 | 34.552 | 21.7494 | 43.6105 | 19.9288 | 42.5819 | 27.45 | 50.242 | 38.5558 |
| SRb | pmol/kg/min | 1.3529 | 1.6791 | 1.4999 | 1.687 | 1.1615 | 1.4634 | 1.1764 | 1.4149 | 1.736 | 1.1567 |

TABLE 3

Model Parameters in 10 Type 2 Diabetic Subjects

| parameter | unit | subj #1 | subj #2 | subj #3 | subj #4 | subj #5 | subj #6 | subj #7 | subj #8 | subj #9 | subj #10 |
|---|---|---|---|---|---|---|---|---|---|---|---|
| kabs | min^-1 | 0.0514 | 0.0276 | 0.0643 | 0.0768 | 0.0276 | 0.0499 | 0.04 | 0.0753 | 0.0188 | 0.1003 |
| kmax | min^-1 | 0.0315 | 0.0594 | 0.0188 | 0.0266 | 0.0593 | 0.0522 | 0.0605 | 0.0149 | 0.059 | 0.0336 |
| kmin | min^-1 | 0.0066 | 0.0041 | 0.007 | 0.0142 | 0.0041 | 0.0119 | 0.0047 | 0.0042 | 0.0057 | 0.0135 |
| b | dimensionless | 0.8244 | 0.5521 | 0.8097 | 0.7339 | 0.5518 | 0.4931 | 0.6156 | 1.018 | 0.4749 | 0.7751 |
| c | dimensionless | 0.1662 | 0.0778 | 0.2434 | 0.0434 | 0.0778 | 0.0231 | 0.1176 | 0.6368 | 0.0409 | 0.0233 |
| ki | min^-1 | 0.0152 | 0.0059 | 0.016 | 0.0118 | 0.0059 | 0.0056 | 0.0072 | 0.0111 | 0.0059 | 0.003 |
| kp2 | min^-1 | 0.0037 | 0.0007 | 0.0053 | 0.0023 | 0.0007 | 0.0008 | 0.0027 | 0.0033 | 0.0009 | 0.0006 |
| kp3 | mg/kg/min/(pmol/l) | 0.0055 | 0.0161 | 0.0052 | 0.0076 | 0.0162 | 0.003 | 0.0054 | 0.0023 | 0.0066 | 0.0064 |
| kp4 | mg/kg/min/(pmol/kg) | 0.0448 | 0.0925 | 0.0214 | 0.073 | 0.0925 | 0.0152 | 0.0656 | 0.0214 | 0.1546 | 0.1207 |
| Vg | dl/kg | 0.7907 | 0.8542 | 0.5878 | 1.7279 | 0.8542 | 1.4555 | 0.9845 | 0.6865 | 0.7526 | 2.4251 |
| Vmx | mg/kg/min per pmol/L | 0.0409 | 0.0363 | 0.0244 | 0.0591 | 0.0363 | 0.017 | 0.0689 | 0.0137 | 0.0274 | 0.054 |
| km0 | mg/kg | 357.0175 | 719.292 | 372.048 | 432.325 | 719.293 | 158.8016 | 331.7172 | 271.744 | 598.0593 | 457.3906 |
| K2 | min^-1 | 0.0272 | 0.0891 | 0.018 | 0.0504 | 0.0887 | 0.0476 | 0.0853 | 0.0335 | 0.0107 | 0.0376 |

TABLE 3-continued

Model Parameters in 10 Type 2 Diabetic Subjects

| parameter | unit | subj #1 | subj #2 | subj #3 | subj #4 | subj #5 | subj #6 | subj #7 | subj #8 | subj #9 | subj #10 |
|---|---|---|---|---|---|---|---|---|---|---|---|
| K1 | min^-1 | 0.0814 | 0.0937 | 0.0906 | 0.0624 | 0.0933 | 0.0484 | 0.0758 | 0.071 | 0.0485 | 0.0194 |
| p2U | min^-1 | 0.0207 | 0.0853 | 0.0164 | 0.1419 | 0.0853 | 0.065 | 0.0131 | 0.0137 | 0.4861 | 0.0471 |
| Vi | l/kg | 0.04 | 0.0385 | 0.0404 | 0.0391 | 0.0385 | 0.0528 | 0.044 | 0.043 | 0.0401 | 0.0394 |
| K | pmol/kg/(mg/dl) | 1.5045 | 0.3015 | 1.5882 | 0.7135 | 0.3012 | 1.918 | 1.3548 | 2.2587 | 0.3735 | 1.4973 |
| β | pmol/kg/min/(mg/dl) | 0.0711 | 0.0122 | 0.0373 | 0.071 | 0.0122 | 0.1722 | 0.1482 | 0.0798 | 0.0425 | 0.1191 |
| α | min^-1 | 0.0127 | 0.0415 | 0.0392 | 0.0182 | 0.0415 | 0.0083 | 0.0082 | 0.0123 | 0.0087 | 0.0067 |
| m1 | min^-1 | 0.3068 | 0.0957 | 0.1807 | 0.5012 | 0.0956 | 0.0391 | 0.3772 | 0.1075 | 0.1218 | 0.1871 |
| m5 | min * kg/pmol | 0.0523 | 0.1129 | 0.0499 | 0.0439 | 0.1129 | 0.0169 | 0.0276 | 0.0354 | 0.0926 | 0.0237 |
| Gb | mg/dl | 141.7659 | 265.4568 | 179.435 | 127.8186 | 265.4568 | 64.313 | 126.1426 | 178.2554 | 178.9323 | 114.0946 |
| EGPb | mg/kg/min | 2.0356 | 2.5077 | 1.6258 | 2.1968 | 2.5077 | 0.8218 | 2.0573 | 1.3879 | 2.0212 | 2.0332 |
| BW | kg | 88.9266 | 106.4649 | 128.5865 | 75.4929 | 106.4648 | 81.3829 | 81.3337 | 129.8287 | 87.0632 | 59.7271 |
| Ib | pmol/l | 27.6839 | 94.1748 | 78.8107 | 20.3449 | 94.1748 | 37.6358 | 32.3702 | 148.7886 | 29.1458 | 42.3448 |
| SRb | pmol/kg/min | 2.4889 | 7.2006 | 3.453 | 1.896 | 7.2004 | 1.659 | 3.3775 | 3.4148 | 3.1313 | 3.6781 |

Table 4 includes the mean, SD, and the range of all model parameters defining the span of the simulated populations:

TABLE 4

Mean, Standard Deviation and the Range of Prediabetic and Type 2 Diabetic Populations

| parameter | unit | Prediabetics | | | Type 2 Diabetics | | |
|---|---|---|---|---|---|---|---|
| | | Mean | SD | range | Mean | SD | range |
| kabs | min^-1 | 0.0883 | 0.0491 | 0.0191 ÷ 0.3564 | 0.0809 | 0.0627 | 0.0154 ÷ 0.2927 |
| kmax | min^-1 | 0.0325 | 0.0088 | 0.0174 ÷ 0.0734 | 0.0435 | 0.0273 | 0.0101 ÷ 0.1853 |
| kmin | min^-1 | 0.0107 | 0.0035 | 0.0050 ÷ 0.0201 | 0.0077 | 0.0033 | 0.0021 ÷ 0.0190 |
| b | dimensionless | 0.7011 | 0.1598 | 0.3538 ÷ 1.2667 | 0.7578 | 0.1849 | 0.4589 ÷ 1.3582 |
| c | dimensionless | 0.0829 | 0.0457 | 0.0194 ÷ 0.2882 | 0.1288 | 0.1113 | 0.0215 ÷ 0.6368 |
| ki | min^-1 | 0.0104 | 0.0044 | 0.0024 ÷ 0.0242 | 0.0086 | 0.0035 | 0.0030 ÷ 0.0187 |
| kp2 | min^-1 | 0.0047 | 0.0029 | 0.0009 ÷ 0.0215 | 0.0025 | 0.0022 | 0.0004 ÷ 0.0101 |
| kp3 | mg/kg/min/(pmol/l) | 0.0078 | 0.0061 | 0.0016 ÷ 0.036 | 0.0062 | 0.0030 | 0.0020 ÷ 0.0162 |
| kp4 | mg/kg/min/(pmol/kg) | 0.0337 | 0.0247 | 0.0072 ÷ 0.112 | 0.0553 | 0.0354 | 0.0081 ÷ 0.1760 |
| Vg | dl/kg | 1.3850 | 0.3900 | 0.7259 ÷ 2.6317 | 1.1908 | 0.5288 | 0.4002 ÷ 3.2804 |
| Vmx | mg/kg/min per pmol/L | 0.0465 | 0.0471 | 0.0044 ÷ 0.3949 | 0.0496 | 0.0558 | 0.0031 ÷ 0.4820 |
| km0 | mg/kg | 220.46 | 42.94 | 143.22 ÷ 326.27 | 388.56 | 154.61 | 142.99 ÷ 925.26 |
| K2 | min^-1 | 0.0825 | 0.0368 | 0.0240 ÷ 0.1982 | 0.1021 | 0.2655 | 0.0035 ÷ 1.4187 |
| K1 | min^-1 | 0.0895 | 0.0192 | 0.0498 ÷ 0.1543 | 0.0570 | 0.0256 | 0.0164 ÷ 0.1214 |
| p2U | min^-1 | 0.0513 | 0.0176 | 0.0157 ÷ 0.1024 | 0.0543 | 0.0611 | 0.0032 ÷ 0.4861 |
| Vi | l/kg | 0.0486 | 0.0028 | 0.0417 ÷ 0.0562 | 0.0425 | 0.0041 | 0.0337 ÷ 0.0539 |
| K | pmol/kg/(mg/dl) | 2.6275 | 1.1470 | 0.7647 ÷ 6.6455 | 1.2288 | 0.4852 | 0.3011 ÷ 2.6059 |
| β | pmol/kg/min/(mg/dl) | 0.1246 | 0.0451 | 0.0610 ÷ 0.3056 | 0.0763 | 0.0468 | 0.0122 ÷ 0.2719 |
| α | min^-1 | 0.0535 | 0.0313 | 0.0151 ÷ 0.1425 | 0.0208 | 0.0123 | 0.0031 ÷ 0.0722 |
| m1 | min^-1 | 0.1657 | 0.0708 | 0.0544 ÷ 0.4519 | 0.1885 | 0.1207 | 0.0391 ÷ 0.6578 |
| m5 | min * kg/pmol | 0.0215 | 0.0096 | 0.0029 ÷ 0.0504 | 0.0446 | 0.0235 | 0.0074 ÷ 0.1129 |
| Gb | mg/dl | 95.60 | 9.31 | 78.49 ÷ 117.21 | 143.82 | 38.71 | 64.31 ÷ 265.46 |
| EGPb | mg/kg/min | 1.3350 | 0.2506 | 0.9019 ÷ 2.1415 | 1.8151 | 0.4213 | 0.8218 ÷ 3.2570 |
| BW | kg | 92.0528 | 20.3911 | 53.1937 ÷ 150.256 | 91.3930 | 21.2427 | 54.6762 ÷ 192.8718 |
| Ib | pmol/l | 38.0648 | 20.4097 | 9.3908 ÷ 143.376 | 52.7363 | 33.7269 | 13.8310 ÷ 187.1251 |
| SRb | pmol/kg/min | 1.4479 | 0.4901 | 0.5841 ÷ 3.3658 | 3.2732 | 1.5889 | 1.0706 ÷ 7.5345 |

Figure 5:
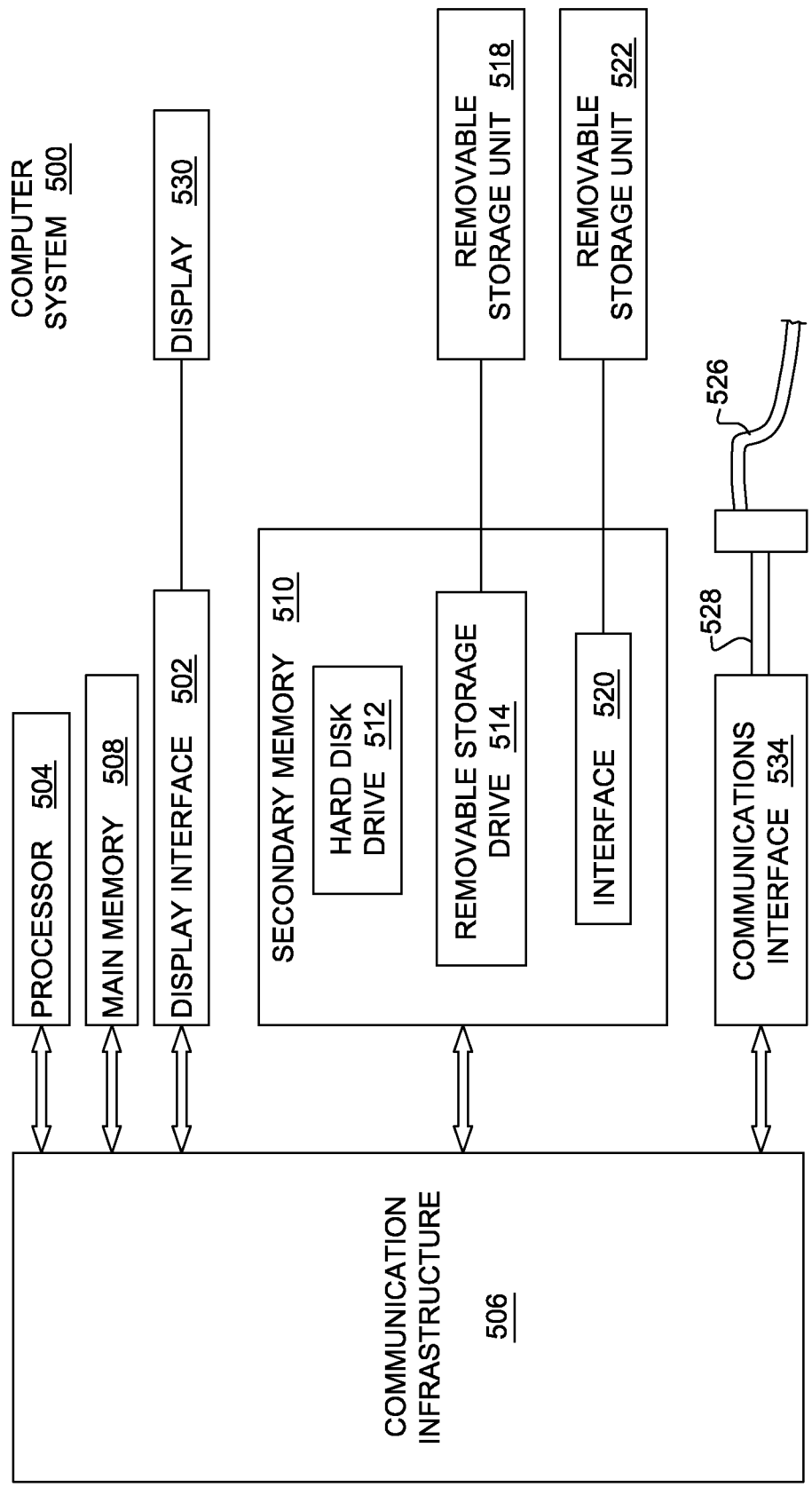
FIG. 5 is a schematic block diagram for a system or related method of an embodiment of the present invention.

FIG. 5 is a functional block diagram for a computer system 500 for implementation of an exemplary embodiment or portion of an embodiment of the present invention. For example, a method or system of an embodiment of the present invention may be implemented using hardware, software or a combination thereof and may be implemented in one or more computer systems or other processing systems, such as personal digit assistants (PDAs) equipped with adequate memory and processing capabilities. In an example embodiment, the invention was implemented in software running on a general purpose computer 50 as illustrated in FIG. 5. The computer system 500 may includes one or more processors, such as processor 504. The Processor 504 is connected to a communication infrastructure 506 (e.g., a communications bus, cross-over bar, or network).

The computer system 500 may include a display interface 502 that forwards graphics, text, and/or other data from the communication infrastructure 506 (or from a frame buffer not shown) for display on the display unit 530. Display unit 530 may be digital and/or analog.

The computer system 500 may also include a main memory 508, preferably random access memory (RAM), and may also include a secondary memory 510. The secondary memory 510 may include, for example, a hard disk drive 512 and/or a removable storage drive 514, representing a floppy disk drive, a magnetic tape drive, an optical disk drive, a flash memory, etc. The removable storage drive 514 reads from and/or writes to a removable storage unit 518 in a well known manner. Removable storage unit 518, represents a floppy disk, magnetic tape, optical disk, etc. which is read by and written to by removable storage drive 514. As will be appreciated, the removable storage unit 518 includes a computer usable storage medium having stored therein computer software and/or data.

In alternative embodiments, secondary memory 510 may include other means for allowing computer programs or other instructions to be loaded into computer system 500. Such means may include, for example, a removable storage unit 522 and an interface 520. Examples of such removable storage units/interfaces include a program cartridge and cartridge interface (such as that found in video game devices), a removable memory chip (such as a ROM, PROM, EPROM or EEPROM) and associated socket, and other removable storage units 522 and interfaces 520 which allow software and data to be transferred from the removable storage unit 522 to computer system 500.

The computer system 500 may also include a communications interface 524. Communications interface 124 allows software and data to be transferred between computer system 500 and external devices. Examples of communications interface 524 may include a modem, a network interface (such as an Ethernet card), a communications port (e.g., serial or parallel, etc.), a PCMCIA slot and card, a modem, etc. Software and data transferred via communications interface 524 are in the form of signals 528 which may be electronic, electromagnetic, optical or other signals capable of being received by communications interface 524. Signals 528 are provided to communications interface 524 via a communications path (i.e., channel) 526. Channel 526 (or any other communication means or channel disclosed herein) carries signals 528 and may be implemented using wire or cable, fiber optics, blue tooth, a phone line, a cellular phone link, an RF link, an infrared link, wireless link or connection and other communications channels.

In this document, the terms "computer program medium" and "computer usable medium" are used to generally refer to media or medium such as various software, firmware, disks, drives, removable storage drive 514, a hard disk installed in hard disk drive 512, and signals 528. These computer program products ("computer program medium" and "computer usable medium") are means for providing software to computer system 500. The computer program product may comprise a computer useable medium having computer program logic thereon. The invention includes such computer program products. The "computer program product" and "computer useable medium" may be any computer readable medium having computer logic thereon.

Computer programs (also called computer control logic or computer program logic) are may be stored in main memory 508 and/or secondary memory 510. Computer programs may also be received via communications interface 524. Such computer programs, when executed, enable computer system 500 to perform the features of the present invention as discussed herein. In particular, the computer programs, when executed, enable processor 504 to perform the functions of the present invention. Accordingly, such computer programs represent controllers of computer system 500.

In an embodiment where the invention is implemented using software, the software may be stored in a computer program product and loaded into computer system 500 using removable storage drive 514, hard drive 512 or communications interface 524. The control logic (software or computer program logic), when executed by the processor 504, causes the processor 504 to perform the functions of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an example software embodiment of the invention, the methods described above may be implemented in SPSS control language or C++ programming language, but could be implemented in other various programs, computer simulation and computer-aided design, computer simulation environment, MATLAB, or any other software platform or program, windows interface or operating system (or other operating system) or other programs known or available to those skilled in the art.

PUBLICATIONS

The following patents, applications and publications as listed below and throughout this document are hereby incorporated by reference in their entirety herein.

The devices, systems, compositions, computer program products, and methods of various embodiments of the invention disclosed herein may utilize aspects disclosed in the following references, applications and patents and which are hereby incorporated by reference herein in their entirety:

1. Tirosh A, Shai I, Tekes-Manova D, Israeli E, Pereg D, Shochat T, Kochba I, Rudich A, the Israeli Diabetes Research Group: Normal fasting plasma glucose levels and type 2 diabetes in young men. N Engl J Med 353:1454-1462, 2005
2. Dinneen S F, Maldonado D 3rd, Leibson C L, Klee G G, Li H, Melton L J 3rd, Rizza R A: Effects of changing diagnostic criteria on the risk of developing diabetes. Diabetes Care 21:1408-1413, 1998
3. Meigs J B, Muller D C, Nathan D M, Blake D R, Andres R: The natural history of progression from normal glucose tolerance to type 2 diabetes in the Baltimore Longitudinal Study of Aging. Diabetes 52:1475-1484, 2003
4. Meigs J B, Nathan D M, D'Agostino R B Sr, Wilson P W: Fasting and postchallenge glycemia and cardiovascular disease risk: the Framingham Offspring Study. Diabetes Care 5:1845-1850, 2002
5. Glucose tolerance and mortality: comparison of WHO and American Diabetes Association diagnostic criteria: the DECODE study group: European Diabetes Epidemiology Group: diabetes epidemiology: collaborative analysis of diagnostic criteria in Europe. Lancet 354:617-621, 1999 Albisser A M, Leibel B S, Ewart T G, Davidovac Z, Botz C K, Zinggg W. An artificial endocrine pancreas. *Diabetes,* 23:389-396, 1974.
6. Bock G., Dalla Man C., Campioni M., Chittilapilly E., Basu R., Toffolo G., C., Rizza R. A. Pathogenesis of prediabetes: mechanisms of fasting and postprandial hyperglycemia in people with impaired fasting glucose and/or impaired glucose tolerance. Diabetes 55:3536-49, 2006.
7. Dalla Man C, Rizza R A, Cobelli C. Meal simulation model of the glucose-insulin system. IEEE Trans Biomed Eng, 54: 1740-49, 2007.
8. Kovatchev B P, Breton M D, Dalla Man C, Cobelli C. In Silica Preclinical Trials: A Proof of Concept in Closed-Loop Control of Type 1 Diabetes. J Diabetes Sci Technol 3: 44-55, 2009.
9. Kovatchev B P, Breton M D, Dalla Man C, Cobelli C. In Silico model and computer simulation environment approximating the human glucose/insulin utilization. Food and Drug Administration Master File MAF 1521, 2008.
10. Kovatchev B P et al. Study of Closed-Loop Glucose Control in Type 1 Diabetes. Food and Drug Administration Investigational Device Exemption G080048, 2008.
11. Basu A, Dalla Man C., Basu, R., Toffolo G., Cobelli C., Rizza R. A. Effects of Type 2 Diabetes on Insulin Secretion, Insulin Action, Glucose Effectiveness and Postprandial Glucose Metabolism. Diabetes Care, 32: 866-72, 2009.
12. International Patent Application Serial No. PCT/US2010/025405, entitled "Method, System and Computer Program Product for CGM-Based Prevention of Hypoglycemia via Hypoglycemia Risk Assessment and Smooth Reduction Insulin Delivery," filed Feb. 25, 2010
13. International Patent Application Serial No. PCT/US2009/065725, filed Nov. 24, 2009, entitled "Method, System, and Computer Program Product for Tracking of Blood Glucose Variability in Diabetes from Data,"
14. PCT/US2008/082063, entitled "Model Predictive Control Based Method for Closed-Loop Control of Insulin Delivery in Diabetes Using Continuous Glucose Sensing", filed Oct. 31, 2008.
15. PCT/US2008/069416, entitled "Method, System and Computer Program Product for Evaluation of Insulin Sensitivity, Insulin/Carbohydrate Ratio, and Insulin Correction Factors in Diabetes from Self-Monitoring Data", filed Jul. 8, 2008.
16. PCT/US2008/067725, entitled "Method, System and Computer Simulation Environment for Testing of Monitoring and Control Strategies in Diabetes," filed Jun. 20, 2008.
17. PCT/US2008/067723, entitled "LQG Artificial Pancreas Control System and Related Method", filed on Jun. 20, 2008.
18. U.S. Ser. No. 12/516,044, filed May 22, 2009, entitled "Method, System, and Computer Program Product for the Detection of Physical Activity by Changes in Heart Rate, Assessment of Fast Changing Metabolic States, and Applications of Closed and Open Control Loop in Diabetes;"
19. PCT/US2007/085588 (not yet published) filed Nov. 27, 2007, entitled "Method, System, and Computer Program Product for the Detection of Physical Activity by Changes in Heart Rate, Assessment of Fast Changing Metabolic States, and Applications of Closed and Open Control Loop in Diabetes;"
20. U.S. Ser. No. 11/943,226, filed Nov. 20, 2007, entitled "Systems, Methods and Computer Program Codes for Recognition of Patterns of Hyperglycemia and Hypoglycemia, Increased Glucose Variability, and Ineffective Self-Monitoring in Diabetes;"
21. U.S. patent application Ser. No. 11/578,831, filed Oct. 18, 2006 entitled "Method, System and Computer Program Product for Evaluating the Accuracy of Blood Glucose Monitoring Sensors/Devices".
22. PCT International Application Serial No. PCT/US2005/013792, filed Apr. 21, 2005, entitled "Method, System, and Computer Program Product for Evaluation of the Accuracy of Blood Glucose Monitoring Sensors/Devices;"
23. PCT International Application Serial No. PCT/US01/09884, filed Mar. 29, 2001, entitled "Method, System, and Computer Program Product for Evaluation of Glycemic Control in Diabetes Self-Monitoring Data;"
24. U.S. Pat. No. 7,025,425 B2 issued Apr. 11, 2006, entitled "Method, System, and Computer Program Product for the Evaluation of Glycemic Control in Diabetes from Self-Monitoring Data;"
25. U.S. patent application Ser. No. 11/305,946 filed Dec. 19, 2005 entitled "Method, System, and Computer Program Product for the Evaluation of Glycemic Control in Diabetes from Self-Monitoring Data" (Publication No. 2006/0094947);
26. PCT International Application Serial No. PCT/US2003/025053, filed Aug. 8, 2003, entitled "Method, System, and Computer Program Product for the Processing of Self-Monitoring Blood Glucose (SMBG) Data to Enhance Diabetic Self-Management;"
27. U.S. patent application Ser. No. 10/524,094 filed Feb. 9, 2005 entitled "Managing and Processing Self-Monitoring Blood Glucose" (Publication No. 2005/214892);
28. U.S. Ser. No. 12/065,257, filed Aug. 29, 2008, entitled "Accuracy of Continuous Glucose Sensors;"
29. PCT International Application Serial No PCT/US2006/033724, filed Aug. 29, 2006, entitled "Method for Improvising Accuracy of Continuous Glucose Sensors and a Continuous Glucose Sensor Using the Same;"
30. U.S. Ser. No. 12/159,891, filed Jul. 2, 2008, entitled "Method, System and Computer Program Product for Evaluation of Blood Glucose Variability in Diabetes from Self-Monitoring Data;"
31. PCT International Application No. PCT/US2007/000370, filed Jan. 5, 2007, entitled "Method, System and Computer Program Product for Evaluation of Blood Glucose Variability in Diabetes from Self-Monitoring Data;"
32. U.S. patent application Ser. No. 11/925,689 and PCT International Patent Application No. PCT/US2007/082744, both filed Oct. 26, 2007, entitled "For Method, System and Computer Program Product for Real-Time Detection of Sensitivity Decline in Analyte Sensors;"
33. U.S. Ser. No. 10/069,674, filed Feb. 22, 2002, entitled "Method and Apparatus for Predicting the Risk of Hypoglycemia;"
34. PCT International Application No. PCT/US00/22886, filed Aug. 21, 2000, entitled "Method and Apparatus for Predicting the Risk of Hypoglycemia;"
35. U.S. Pat. No. 6,923,763 B1, issued Aug. 2, 2005, entitled "Method and Apparatus for Predicting the Risk of Hypoglycemia;"
36. U.S. Patent Application No. US 2004/0254434 A1, "Glucose Measuring Module and "Insulin Pump Combination", Dec. 16, 2004.
37. U.S. Patent Application Publication No. US 2009/00697456 A1, Estes, et al., "Operating an Infusion Pump System", Mar. 12, 2009.
38. International Patent Application Serial No. PCT/US2010/036629
Title: System Coordinator and Modular Architecture for Open-Loop and Closed-Loop Control of Diabetes, Filed May 28, 2010.

What is claimed is:

1. An electronic system that simulates a glucose-insulin metabolic system of a T2DM or prediabetic subject, comprising:
a subsystem that models dynamic glucose concentration in a T2DM or prediabetic subject, including:
an electronic module that models endogenous glucose production (EGP(t)) of a T2DM or prediabetic subject,
an electronic module that models meal glucose rate of appearance (Ra(t)) of a T2DM or prediabetic subject, an electronic module that models glucose utilization (U(t)) of a T2DM or prediabetic subject, an electronic module that models renal excretion of glucose (E(t)) of a T2DM or prediabetic subject;

a subsystem that models dynamic insulin concentration in said T2DM or prediabetic subject, including:

an electronic module that models insulin secretion (S(t)) of a T2DM or prediabetic subject;

an electronic database containing a population of virtual T2DM or prediabetic subjects representative of the T2DM and prediabetic population, each virtual subject having a plurality of metabolic parameters with values encompassing a distribution of parameters observed in vivo across the population of T2DM or prediabetic subjects; and a processor that calculates an effect of variation of at least one metabolic parameter value on the glucose-insulin metabolic system of a virtual T2DM or prediabetic subject by inputting said plurality of metabolic parameter values of said T2DM or prediabetic subject into said glucose concentration and insulin concentration subsystems and varying at least one of said metabolic parameter values to determine its effect on the glucose-insulin metabolic system of said T2DM or prediabetic subject.

2. An electronic system as set forth in claim 1, wherein said glucose concentration subsystem models T2DM or prediabetic glucose concentration G(t) in accordance with the following equations:

$$\begin{cases} \dot{G}_p(t) = EGP(t) + Ra(t) - U_{ii}(t) - E(t) - & G_p(0) = G_{pb} \\ k_1 \cdot G_p(t) + k_2 \cdot G_t(t) & \\ \dot{G}_t(t) = -U_{id}(t) + k_1 \cdot G_p(t) - k_2 \cdot G_t(t) & G_t(0) = G_{tb} \\ G(t) = \dfrac{G_p}{V_G} & G(0) = G_b \end{cases}$$

3. An electronic system as set forth in claim 2, wherein said EGP electronic module models EGP(t) according to the equation:

$$EGP(t) = k_{p1} - k_{p2} \cdot G_p(t) - k_{p3} \cdot I_d(t) - k_{p4} \cdot I_{po}(t)$$
$$EGP(0) = EGP_b.$$

4. An electronic system as set forth in claim 3, wherein $i_d$(pmol/l) is a delayed insulin signal realized with a chain of two compartments:

$$\begin{cases} \dot{I}_1(t) = -k_i \cdot [I_1(t) - I(t)] & I_1(0) = I_b \\ \dot{I}_d(t) = -k_i \cdot [I_d(t) - I_1(t)] & I_d(0) = I_b \end{cases}.$$

5. An electronic system as set forth in claim 3, wherein at basal steady state $$k_{p1} = EGP_b + k_{p2} \cdot G_{pb} + k_{p3} \cdot I_b + k_{p4} \cdot I_{pob}.$$

6. An electronic system as set forth in claim 2, wherein said glucose rate of appearance electronic module models Ra(t) according to the equations:

$$\begin{cases} Q_{sto}(t) = Q_{sto1}(t) + Q_{sto2}(t) & Q_{sto}(0) = 0 \\ \dot{Q}_{sto1}(t) = -k_{gri} \cdot Q_{sto1}(t) + D \cdot \delta(t) & Q_{sto1}(0) = 0 \\ \dot{Q}_{sto2}(t) = -k_{empt}(Q_{sto}) \cdot Q_{sto2}(t) + k_{gri} \cdot Q_{sto1}(t) & Q_{sto2}(0) = 0 \\ \dot{Q}_{gut}(t) = -k_{abs} \cdot Q_{gut}(t) + k_{empt}(Q_{sto}) \cdot Q_{sto2}(t) & Q_{gut}(0) = 0 \\ Ra(t) = \dfrac{f \cdot k_{abs} \cdot Q_{gut}(t)}{BW} & Ra(0) = 0 \end{cases}.$$

7. An electronic system as set forth in claim 2, wherein said glucose utilization electronic module models U(t) as the sum of insulin-independent utilization $U_{ii}(t) = F_{cns}$, and insulin-dependent utilization $$U_{id}(t) = \frac{V(X(t)) \cdot G_t(t)}{K_{m0} + G_t(t)}.$$

8. An electronic system as set forth in claim 7, wherein Vm(X(t)) is assumed to be linearly dependent from a remote insulin, X(t):

$$V_m(X(t)) = V_{m0} + V_{mx} \cdot X(t).$$

9. An electronic system as set forth in claim 8, wherein X (pmol/L) is insulin in the interstitial fluid described by:

$$\dot{X}(t) = -p_{2U} \cdot X(t) + p_{2U}[I(t) - I_b] \; X(0) = 0.$$

10. An electronic system as set forth in claim 2, wherein said renal excretion electronic module models renal excretion of glucose E(t) as:

$$E(t) = \begin{cases} k_{e1} \cdot [G_p(t) - k_{e2}] & \text{if } G_p(t) > k_{e2} \\ 0 & \text{if } G_p(t) \leq k_{e2} \end{cases}.$$

11. An electronic system as set forth in claim 1, wherein said insulin concentration subsystem models T2DM or prediabetic insulin concentration I(t) in accordance with the following equations:

$$\begin{cases} \dot{I}_l(t) = -(m_1 + m_3(t)) \cdot I_l(t) + m_2 I_p(t) + S(t) & I_l(0) = I_{lb} \\ \dot{I}_p(t) = -(m_2 + m_4) \cdot I_p(t) + m_1 \cdot I_l(t) & I_p(0) = I_{pb} \\ I(t) = \dfrac{I_p}{V_I} & I(0) = I_b \end{cases}.$$

12. An electronic system as set forth in claim 11, wherein said insulin secretion electronic module models insulin secretion S(t) as:

$$S(t) = \gamma \cdot I_{po}(t), \text{ wherein}$$

$$\dot{I}_{po}(t) = -\gamma \cdot I_{po}(t) + S_{po}(t) \quad I_{po}(0) = I_{pob}$$

$$S_{po}(t) = \begin{cases} Y(t) + K \cdot \dot{G}(t) + S_b & \text{for } \dot{G} > 0 \\ Y(t) + S_b & \text{for } \dot{G} \leq 0 \end{cases}$$

and $$\dot{Y}(t) = \begin{cases} -\alpha \cdot [Y(t) - \beta \cdot (G(t) - h)] & \text{if } \beta \cdot (G(t) - h) \geq -S_b \\ -\alpha \cdot Y(t) - \alpha \cdot S_b & \text{if } \beta \cdot (G(t) - h) < -S_b \end{cases};$$

$$Y(0) = 0.$$

13. An electronic system as set forth in claim 1, wherein a prediabetic subject is a subject with impaired fasting glucose (IFG).

14. An electronic system as set forth in claim 1, wherein a prediabetic subject is a subject with impaired glucose tolerance (IGT).

15. An electronic system as set forth in claim 1, wherein said plurality of metabolic parameters for each virtual subject includes at least one of the following parameters:
$k_{abs}$=rate constant of glucose absorption by the intestine,
$k_{max}$=maximum rate constant of gastric emptying,
$k_{min}$=minimum rate constant of gastric emptying,
b=percentage of the dose for which $k_{empt}$ decreases at $(k_{max}-k_{min})/2$,
c=percentage of the dose for which $k_{empt}$ is back to $(k_{max}-k_{min})/2$,
$k_i$=rate parameter accounting for delay between insulin signal and insulin action on the liver,
$k_{p2}$=liver glucose effectiveness,
$k_{p3}$=parameter governing amplitude of insulin action on the liver,
$k_g$=parameter governing amplitude of portal insulin action on the liver,
$V_g$=distribution volume of glucose,
$V_{mx}$=parameter governing amplitude of insulin action on glucose utilization,
$k_{m0}$=parameter governing glucose control on glucose utilization,
$K_2$=rate parameter accounting for glucose transit from tissue to plasma,
$K_1$=rate parameter accounting for glucose transit from plasma to tissue,
$p_{2U}$=rate parameter accounting for delay between insulin signal and insulin action on glucose utilization,
$V_i$=distribution volume of insulin,
K=beta-cell responsivity to glucose rate of change,
β=beta-cell responsivity to glucose level,
α=rate parameter accounting for delay between glucose signal and insulin secretion,
$m_1$=rate parameter of insulin kinetics,
$m_s$=coefficient linking insulin hepatic extraction to insulin secretion rate,
$G_b$=basal plasma glucose concentration,
$EGP_b$=basal endogenous glucose production,
BW=body weight,
$I_b$=basal plasma insulin concentration, and
$SR_b$=basal insulin secretion rate.

16. An electronic system as set forth in claim 1, wherein said subsystems and modules are implemented as computer-executable software stored on a computer-readable storage medium and loaded into an electronic programmable computer.

17. An electronic system as set forth in claim 1, wherein said subsystems and modules are implemented as application specific integrated circuit modules.

18. A computer-executable program product comprising computer executable code stored in a non-transitory computer-readable storage medium, wherein said computer-executable program product simulates a glucose-insulin metabolic system of a T2DM or prediabetic subject, said computer-executable code comprising:
subsystem code that models dynamic glucose concentration in a T2DM or prediabetic subject, including:
an electronic code module that models endogenous glucose production (EGP(t)) of a T2DM or prediabetic subject,
an electronic code module that models meal glucose rate of appearance (Ra(t)) of a T2DM or prediabetic subject,
an electronic code module that models glucose utilization (U(t)) of a T2DM or prediabetic subject,
an electronic code module that models renal excretion of glucose (E(t)) of a T2DM or prediabetic subject;
subsystem code that models dynamic insulin concentration in said T2DM or prediabetic subject, including:
an electronic code module that models insulin secretion (S(t)) of a T2DM or prediabetic subject;
an electronic database containing a population of virtual T2DM or prediabetic subjects representative of the T2DM and prediabetic population, each virtual subject having a plurality of metabolic parameters with values encompassing a distribution of parameters observed in vivo across the population of T2DM or prediabetic subjects; and
computer-executable code that calculates an effect of variation of at least one metabolic parameter value on the glucose-insulin metabolic system of a virtual T2DM or prediabetic subject by inputting said plurality of metabolic parameter values of said T2DM or prediabetic subject into said glucose concentration and insulin concentration subsystems and varying at least one of said metabolic parameter values to determine its effect on the glucose-insulin metabolic system of said T2DM or prediabetic subject.

19. A computer-executable program product as set forth in claim 18, wherein said glucose concentration subsystem code models T2DM or prediabetic glucose concentration G(t) in accordance with the following equations:

$$\begin{cases} \dot{G}_p(t) = EGP(t) + Ra(t) - U_{ii}(t) - E(t) - & G_p(0) = G_{pb} \\ k_1 \cdot G_p(t) + k_2 \cdot G_t(t) \\ \dot{G}_t(t) = -U_{id}(t) + k_1 \cdot G_p(t) - k_2 \cdot G_t(t) & G_t(0) = G_{tb} \\ G(t) = \dfrac{G_p}{V_G} & G(0) = G_b \end{cases}$$

20. A computer-executable program product as set forth in claim 19, wherein said EGP code module models EGP(t) according to the equation:

$$EGP(t)=k_{p1}-k_{p2}\cdot G_p(t)-k_{p3}\cdot I_d(t)-k_{p4}\cdot I_{po}(t)$$
$$EGP(0)=EGP_b.$$

21. A computer-executable program product as set forth in claim 20, wherein $I_d$ (pmol/l) is a delayed insulin signal realized with a chain of two compartments:

$$\begin{cases} \dot{I}_1(t) = -k_i \cdot [I_1(t) - I(t)] & I_1(0) = I_b \\ \dot{I}_d(t) = -k_i \cdot [I_d(t) - I_1(t)] & I_d(0) = I_b \end{cases}$$

22. A computer-executable program product as set forth in claim 20, wherein at basal steady state $$k_{p1}=EGP_b+k_{p2}\cdot G_{pb}+k_{p3}\cdot I_b+k_{p4}\cdot I_{pob}.$$

23. A computer-executable program product as set forth in claim 19, wherein said glucose rate of appearance code module models Ra(t) according to the equations:

$$\begin{cases} Q_{sto}(t) = Q_{sto1}(t) + Q_{sto2}(t) & Q_{sto}(0) = 0 \\ \dot{Q}_{sto1}(t) = -k_{gri} \cdot Q_{sto1}(t) + D \cdot \delta(t) & Q_{sto1}(0) = 0 \\ \dot{Q}_{sto2}(t) = -k_{empt}(Q_{sto}) \cdot Q_{sto2}(t) + k_{gri} \cdot Q_{sto1}(t) & Q_{sto2}(0) = 0 \\ \dot{Q}_{gut} = -k_{abs} \cdot Q_{gut}(t) + k_{empt}(Q_{sto}) \cdot Q_{sto2}(t) & Q_{gut}(0) = 0 \\ Ra(t) = \dfrac{f \cdot k_{abs} \cdot Q_{gut}(t)}{BW} & Ra(0) = 0 \end{cases}.$$

24. A computer-executable program product as set forth in claim 19, wherein said glucose utilization code module models U(t) as the sum of insulin-independent utilization $U_{ii}(t) = F_{cns}$, and insulin-dependent utilization $$U_{id}(t) = \frac{V(X(t)) \cdot G_t(t)}{K_{m0} + G_t(t)}.$$

25. A computer-executable program product as set forth in claim 24, wherein Vm(X(t)) is assumed to be linearly dependent from a remote insulin, X(t):

$$V_m(X(t)) = V_{m0} + V_{mx} \cdot X(t).$$

26. A computer-executable program product as set forth in claim 25, wherein X (pmol/L) is insulin in the interstitial fluid described by:

$$\dot{X}((t) = -p_{2U} \cdot X(t) + p_{2U}[I(t) - I_b] \quad X(0) = 0.$$

27. A computer-executable program product as set forth in claim 18, wherein said renal excretion code module models renal excretion of glucose E(t) as:

$$E(t) = \begin{cases} k_{e1} \cdot [G_p(t) - k_{e2}] & \text{if } G_p(t) > k_{e2} \\ 0 & \text{if } G_p(t) \le k_{e2} \end{cases}.$$

28. A computer-executable program product as set forth in claim 18, wherein said insulin concentration subsystem code models T2DM or prediabetic insulin concentration I(t) in accordance with the following equations:

$$\begin{cases} \dot{I}_l(t) = -(m_1 + m_3(t)) \cdot I_l(t) + m_2 I_p(t) + S(t) & I_l(0) = I_{lb} \\ \dot{I}_p(t) = -(m_2 + m_4) \cdot I_p(t) + m_1 \cdot I_l(t) & I_p(0) = I_{pb} \\ I(t) = \dfrac{I_p}{V_I} & I(0) = I_b \end{cases}.$$

29. A computer-executable program product as set forth in claim 28, wherein said insulin secretion code module models insulin secretion S(t) as:

$$S(t) = \gamma \cdot I_{po}(t), \text{ wherein}$$

$$\dot{I}_{po}(t) = -\gamma \cdot I_{po}(t) + S_{po}(t) \quad I_{po}(0) = I_{pob}$$

$$S_{po}(t) = \begin{cases} Y(t) + K \cdot \dot{G}(t) + S_b & \text{for } \dot{G} > 0 \\ Y(t) + S_b & \text{for } \dot{G} \le 0 \end{cases}$$

and $$\dot{Y}(t) = \begin{cases} -\alpha \cdot [Y(t) - \beta \cdot (G(t) - h)] & \text{if } \beta \cdot (G(t) - h) \ge -S_b \\ -\alpha \cdot Y(t) - \alpha \cdot S_b & \text{if } \beta \cdot (G(t) - h) < -S_b \end{cases}.$$

$$Y(0) = 0.$$

30. A computer-executable program product as set forth in claim 18, wherein a prediabetic subject is a subject with impaired fasting glucose (IFG).

31. A computer-executable program product as set forth in claim 18, wherein a prediabetic subject is a subject with impaired glucose tolerance (IGT).

32. A computer-executable program product as set forth in claim 18, wherein said plurality of metabolic parameters for each virtual subject includes at least one of the following parameters:

$k_{abs}$=rate constant of glucose absorption by the intestine,
$k_{max}$=maximum rate constant of gastric emptying,
$k_{min}$=minimum rate constant of gastric emptying,
b=percentage of the dose for which $k_{empt}$ decreases at $(k_{max}-k_{min})/2$,
c=percentage of the dose for which $k_{empt}$ is back to $(k_{max}-k_{min})/2$,
$k_i$=rate parameter accounting for delay between insulin signal and insulin action on the liver,
$k_{p2}$=liver glucose effectiveness,
$k_{p3}$=parameter governing amplitude of insulin action on the liver,
$k_{p4}$=parameter governing amplitude of portal insulin action on the liver,
$V_g$=distribution volume of glucose,
$V_{mx}$=parameter governing amplitude of insulin action on glucose utilization,
$k_{m0}$=parameter governing glucose control on glucose utilization,
$K_2$=rate parameter accounting for glucose transit from tissue to plasma,
$K_1$=rate parameter accounting for glucose transit from plasma to tissue,
$p_{2U}$=rate parameter accounting for delay between insulin signal and insulin action on glucose utilization,
$V_i$=distribution volume of insulin,
K=beta-cell responsivity to glucose rate of change,
β=beta-cell responsivity to glucose level,
α=rate parameter accounting for delay between glucose signal and insulin secretion,
$m_1$=rate parameter of insulin kinetics,
$m_s$=coefficient linking insulin hepatic extraction to insulin secretion rate,
$G_b$=basal plasma glucose concentration,
$EGP_b$=basal endogenous glucose production,
BW=body weight,
$I_b$=basal plasma insulin concentration, and
$SR_b$=basal insulin secretion rate.

\* \* \* \* \*

UNITED STATES PATENT AND TRADEMARK OFFICE
CERTIFICATE OF CORRECTION

PATENT NO. : 11,238,990 B2
APPLICATION NO. : 13/380839
DATED : February 1, 2022
INVENTOR(S) : Kovatchev et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1473 days.

Signed and Sealed this
Twenty-ninth Day of November, 2022

Katherine Kelly Vidal
*Director of the United States Patent and Trademark Office*